US008558002B2

(12) United States Patent
Boral et al.

(10) Patent No.: US 8,558,002 B2
(45) Date of Patent: Oct. 15, 2013

(54) SULFOXIMINES AS KINASE INHIBITORS

(75) Inventors: Sougato Boral, Irvine, CA (US); Shimiao Wang, Tustin, CA (US); Julie A. Wurster, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/277,842

(22) Filed: Oct. 20, 2011

(65) Prior Publication Data

US 2012/0196902 A1 Aug. 2, 2012

Related U.S. Application Data

(63) Continuation-in-part of application No. 12/319,356, filed on Jan. 5, 2009, now Pat. No. 8,143,410, which is a continuation-in-part of application No. 11/941,753, filed on Nov. 16, 2007, now Pat. No. 7,915,443.

(60) Provisional application No. 60/866,080, filed on Nov. 16, 2006.

(51) Int. Cl.
| C07D 241/00 | (2006.01) |
| C07D 211/72 | (2006.01) |
| A61K 31/497 | (2006.01) |
| A61K 31/44 | (2006.01) |

(52) U.S. Cl.
USPC ......... 546/316; 544/336; 514/252.1; 514/355

(58) Field of Classification Search
None
See application file for complete search history.

(56) References Cited

U.S. PATENT DOCUMENTS

| 4,556,413 A | 12/1985 | Frater et al. |
| 2008/0241252 A1 | 10/2008 | Lyons et al. |

FOREIGN PATENT DOCUMENTS

| EP | 0023392 | 2/1981 |
| EP | 0109575 | 5/1984 |
| EP | 0673930 A1 | 3/1995 |
| EP | 673930A1 A1 | 3/1995 |
| WO | WO 00/27823 | 5/2000 |
| WO | WO 02/50071 | 6/2002 |
| WO | WO0250071 | 6/2002 |
| WO | WO 2004/014300 | 2/2004 |
| WO | WO 2005/037800 | 4/2005 |
| WO | 2005-060970 | 7/2005 |
| WO | WO 2005/107708 A1 | 11/2005 |
| WO | WO 2006/044823 | 4/2006 |
| WO | WO 2006/082373 | 8/2006 |
| WO | WO 2006/082404 | 8/2006 |
| WO | WO 2006/099974 | 9/2006 |
| WO | WO2006101860 | 9/2006 |
| WO | WO 2006/103449 | 10/2006 |
| WO | WO 2007/075869 | 7/2007 |
| WO | WO 2008/061236 A2 | 5/2008 |
| WO | WO2009064251 A1 | 5/2009 |

OTHER PUBLICATIONS

Silva, A. et al., Mini-Reviews in Medicinal Chemistry, 2005, vol. 5, pp. 893-914.*
Asoka, Y., et al., Exp. Op. Investig. Drugs vol. 20, 2011 pp. 1-10.
Baranda, J., et al., Exp. Op. Invetig. Drugs vol. 16, 2007, pp. 311-324.
Campochiaro, "Molecular Targets for Retinal Vascular Diseases," Journal of Cellular Physiology 210:575-581 (2007).
Database online, "Pyridyloxybenzamide derivatives as herbicides", XP002477770, STN-522316-1983.
Database Chemcats, "Interchim Intermediates", XP002477771, 2035822323, 2007.
Ho, C., et al., Exp. Op Investig. Drugs vol. 18, 2009 pp. 1133-1145.
Hcaplus 1975:139783, "N-9o- and p-nitrobenzoyl)-sufoximine intermediates", Hermann et. al., 1975.
Hcaplus 1974:504104, "Rearrangement processes in the mass spectra of N-substituted sulfoximines", Whittle et. al., 1974.
Hcaplus 1984:610736 abstract, "Benzoic acid derivatives," Frater, et al., 1984.
Ishihara et al, "Preparation of benzylamine derivatives having excellent ileal bile acid transporter inhibitory activity", Chemical Abstracts Service—XP002477766, 1999.
Jabbour, et al., Exp. Op. Investig. Drugs vol. 17, 2008, pp. 1127-1136.
Konishi et al, "Preparation of styrenecarboxamides as leukotriene antagonists", STN—XP002477769, STN-191363-1994.
Matsusawa et al, "Heat-sensitive recording materials containing specific recording materials containing specific color-developing materials", XP002477768, STN-547198-2002.
Patani et al., "Biososterism: A Rational Approach in Drug Design", Chem. Rev. 1996, pp. 3147-3176.
Suzuki et al, "Preparation of benzene derivatives containing amide moiety as ACC inhibitors activity", XP002477767, STN-1216425-2005.
International Search Report for PCT/US2009/069774, Mar. 29, 2010.
Bolm, Carsten et al, Palladium-catalyzed intramolecular a-arylation of sulfoximines, Journal of Organometallic Chemistry, 2003, Journal of Organometallic Chemistry (2003), 6872) 444-450 CODEN: JORCAI; ISSN: 0022-328X; CASREACT 140:163801, Elsevier Science B.V., DE.

* cited by examiner

*Primary Examiner* — Janet Andres
*Assistant Examiner* — Heidi Reese
(74) *Attorney, Agent, or Firm* — Krishna G. Banerjee

(57) ABSTRACT

The present invention relates to organic molecules capable of modulating tyrosine kinase signal transduction in order to regulate, modulate and/or inhibit abnormal cell proliferation.

35 Claims, No Drawings

SULFOXIMINES AS KINASE INHIBITORS

CROSS REFERENCE TO RELATED APPLICATIONS

This application is a continuation in part of U.S. patent application Ser. No. 12/319,356, which was filed on Jan. 5, 2009 now U.S. Pat. No. 8,143,410, in the names of Spada, et al., which is a continuation in part of U.S. patent application Ser. No. 11/941,753, now U.S. Pat. No. 7,915,443, which was filed on Nov. 16, 2007, in the names of Spada et. al, which is based on, and claims the benefit of, U.S. Provisional Application No. 60/866,080, filed Nov. 16, 2006, all of which patent applications are incorporated herein by reference.

BACKGROUND OF THE INVENTION

1. Field of the Invention

The present invention relates to novel compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic disorders and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phosphorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-$\alpha$, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF $\alpha$ and $\beta$ receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fins-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334-339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lek, Blk, Hck, Fgr and Yrk. The Src subfamily of enzymes has been linked to oncogenesis. A more detailed discussion of non-receptor tyrosine kinases is provided in Bolen, 1993, Oncogen 8: 2025-2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat.

No. 4,966,849), soluble receptors and antibodies (PCT Application No. WO 94/10202; Kendall & Thomas, 1994, Proc. Nat'l Acad. Sci. 90: 10705-09; Kim, et al, 1993, Nature 362: 841-844), RNA ligands (Jellinek, et al, Biochemistry 33: 10450-56); Takano, et al, 1993, Mol. Bio. Cell 4:358 A; Kinsella, et al, 1992, Exp. Cell Res. 199: 56-62; Wright, et al, 1992, J. Cellular Phys. 152: 448-57) and tyrosine kinase inhibitors (PCT Application Nos. WO 94/03427; WO 92/21660; WO 91/15495; WO 94/14808; U.S. Pat. No. 5,330, 992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinylene-azaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302, 606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

In addition, certain small compounds are disclosed in U.S. Pat. Nos. 5,792,783; 5,834,504; 5,883,113; 5,883,116 and 5,886,020 as useful for the treatment of diseases related to unregulated TKS transduction. See also patents and PCT Published Patent Application WO 02/29630; U.S. Pat. Nos. 6,599,173; 6,765,012; 6,699,863; 6,541,504 and 6,747,025. These patents are hereby incorporated by reference in its entirety for the purpose of disclosing starting materials and methods for the preparation thereof, screens and assays to determine a claimed compound's ability to modulate, regulate and/or inhibit cell proliferation, indications which to are treatable with said compounds, formulations and routes of administration, effective dosages, etc.

BRIEF SUMMARY OF THE INVENTION

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, pterigium autoimmune diseases and transplant rejection.

In one illustrative embodiment, the compounds of the present invention have the following general formula I:

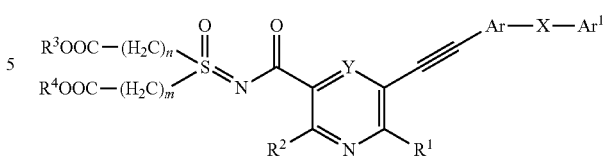

Wherein $R^1$ is hydrogen or $NH_2$ $R^2$ is hydrogen or $NH_2$

X is

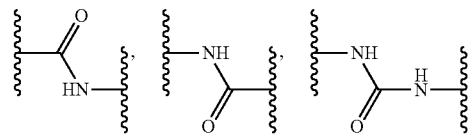

Y is CH or N,

Ar is an aryl group, i.e. a carbocyclic aryl or heteroaryl group, wherein said carbocyclic aryl or heteroaryl group may be optionally substituted with, halogen, alkyl, alkoxy or alkoxycarbonyl, $Ar^1$ is an aryl group, i.e. a carbocyclic aryl or heteroaryl group, wherein said carbocyclic aryl or heteroaryl group may be optionally substituted with halogen, alkyl, alkoxy, alkoxycarbonyl, sulfinyl, thioether, or fluoro or chloro-substituted lower alkyl, $R^3$ is hydrogen or lower alkyl, $R^4$ is hydrogen or lower alkyl, n is an integer of from 1 to 6, m is an integer of from 1 to 6 and prodrugs, pharmaceutically acceptable salts, racemic mixtures and enantiomers of said compound.

Preferably, the compounds of this invention are represented by the general formula II, below:

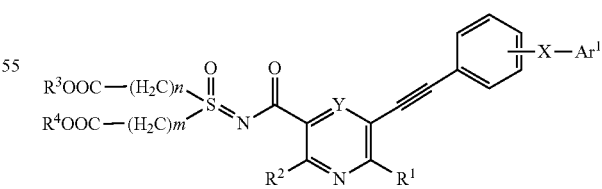

Wherein $R^1$ is hydrogen or $NH_2$ $R^2$ is hydrogen or $NH_2$

X is

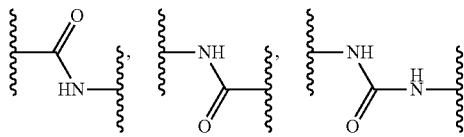

Y is CH or N,
Ar¹ is an aryl group, i.e. a carbocyclic aryl or heteroaryl group, wherein said carbocyclic aryl or heteroaryl group may be optionally substituted with, halogen, alkyl, alkoxy, alkoxycarbonyl, sulfinyl, thioether, or fluoro or chloro lower alkyl,
$R^3$ is hydrogen or lower alkyl,
$R^4$ is hydrogen or lower alkyl,
n is an integer of from 1 to 6,
m is an integer of from 1 to 6 and prodrugs, pharmaceutically acceptable salts, racemic mixtures and enantiomers of said compounds.
Preferably R¹ is $NH_2$
Preferably $R^2$ is hydrogen.
Preferably $R^3$ is hydrogen or methyl,
Preferably $R^4$ is hydrogen or methyl,
Preferably n is an integer of 1 or 4,
Preferably m is an integer of 1 or 4,
Preferably Y is CH,
Preferably Ar¹ is selected from the group consisting of phenyl, furanyl and pyrrolyl, which may be optionally substituted with halogen, lower alkyl or halogen-substituted lower alkyl.
More preferably the substituent may be selected from the group consisting of methyl, fluoro, chloro and trifluoromethyl.

Compounds of formula I and II are useful as kinase inhibitors. As such, compounds of formula I and II will be useful for treating diseases related to unregulated tyrosine kinase signal transduction, for example, cancer, blood vessel proliferative disorders, fibrotic disorders, and neurodegenerative diseases. In particular compounds of the present invention are useful for treatment of mesangial cell proliferative disorders and metabolic diseases, diabetic retinopathy, age-related macular degeneration, retinopathy of prematurity, pterigium, arthritis, restenosis, hepatic cirrhosis, atherosclerosis, psoriasis, diabetis mellitus, wound healing, inflammation and neurodegenerative diseases.

DETAILED DESCRIPTION OF THE INVENTION

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

The following defined terms are used throughout this specification:

"Ac" refers to acetyl
"BOP" refers to (Benzotriazol-1-yloxy)tris(dimethylamino)phosphonium hexafluorophosphate
"DCE" refers to dichloroethane
"DIPEA" refers to N,N-diisopropylethylamine
"DMF" refers to dimethylformamide
"EDC" refers to 1-ethyl-3-(3-dimethyllaminopropypearbodiimide
"Et" refers to ethyl.
"$Et_2O$" refers to diethyl ether
"HMPA" refers to hexamethylphosphorous triamide
"iPr" refers to i-propyl
"Me" refers to methyl.
"MeOH" refers to methanol
"PBS" refers to phosphate buffered saline
"Ph" refers to phenyl
"PPTS" refers to pyridinium p-toluenesulfonate
"PTK" refers to protein tyrosine kinase"
"RTK" refers to receptor tyrosine kinase"
"TBAF" refers to tetrabutylammonium fluoride
"tBu" refers to t-butyl.
"TMS" refers to tetramethylsilane
"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts may also refers to those salts which retain the biological effectiveness and properties of the free acid and which are obtained by reaction with inorganic bases such as sodium hydroxide, calcium hydroxide, magnesium hydroxide, zinc hydroxide or by organic bases such as tromethamine, choline, diethylamine and lysine and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Alkoxy" refers to O-alkyl.
"Alkoxycarbonyl" refers to —C(O)O-alkyl or —C(O)O-aryl.
"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, $NO_2$, amine, thioether, cyano, alkoxy, alkyl, and amino.

"Carbocyclic aryl" refers to an aryl group wherein the ring atoms are carbon.

"Heteroaryl" refers to an aryl group having from 1 to 3 heteroatoms as ring atoms, the remainder of the ring atoms being carbon. Heteroatoms include oxygen, sulfur, and nitrogen. Thus, heteroaryl groups include furanyl, thienyl, pyridyl, pyrrolyl, N-lower alkyl pyrrolo, pyrimidyl, pyrazinyl, imidazolyl and the like.

"Thioether" refers to —S— alkyl, or S— aryl.
"Sulfinyl" refers to —S(O)-alkyl or —S(O)-aryl,
The compounds of this invention may be prepared by the general scheme set forth in Schemes 1-6,

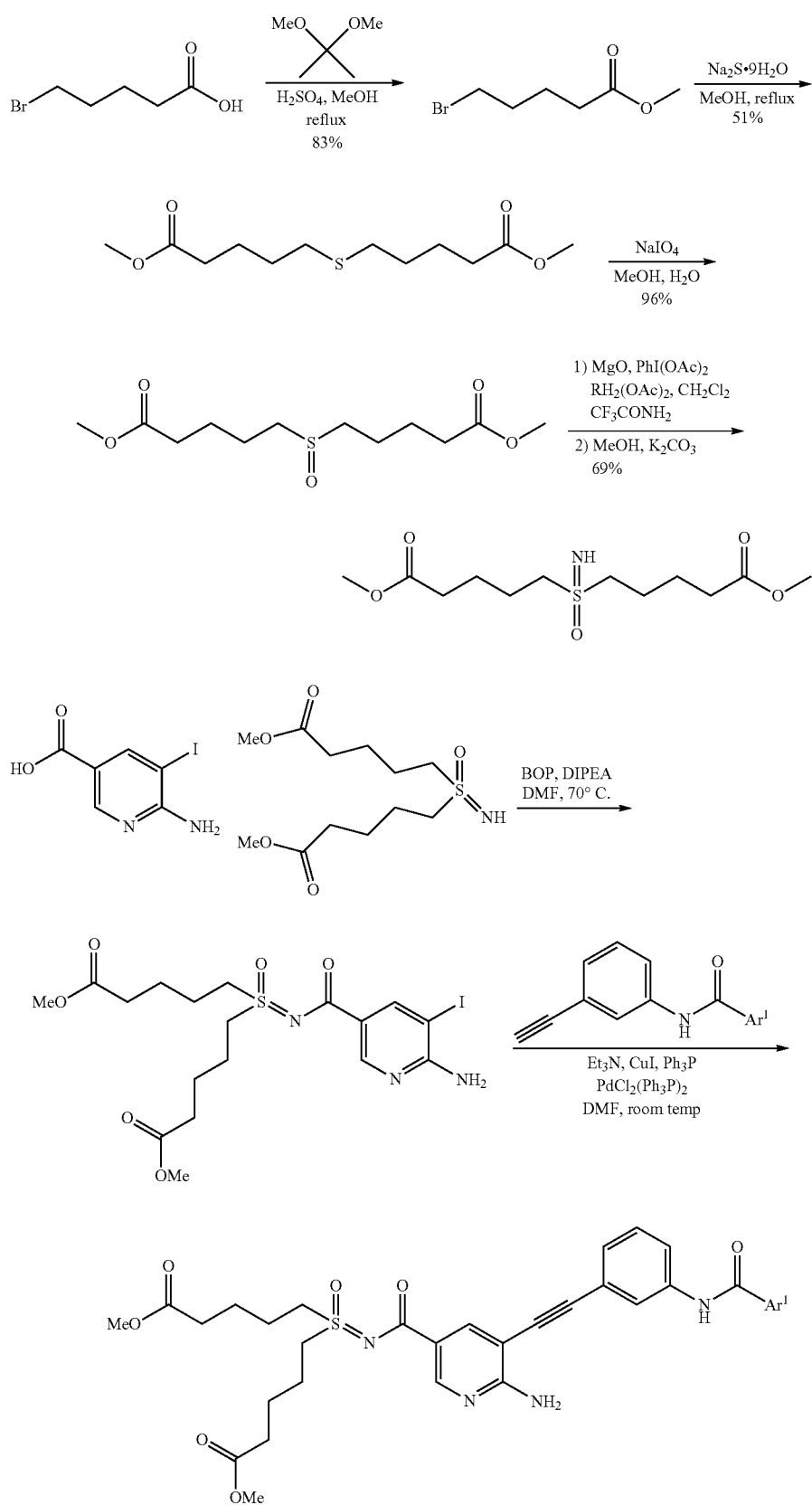

Scheme 2
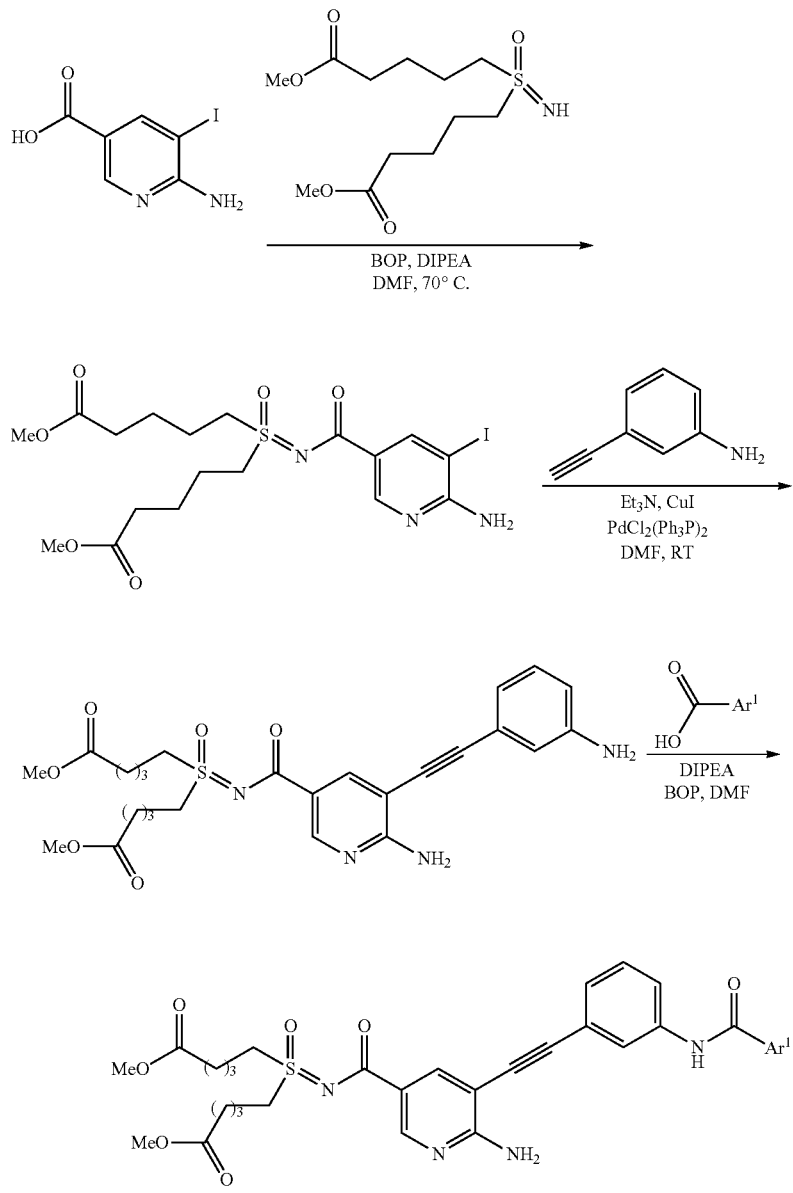
Scheme 3
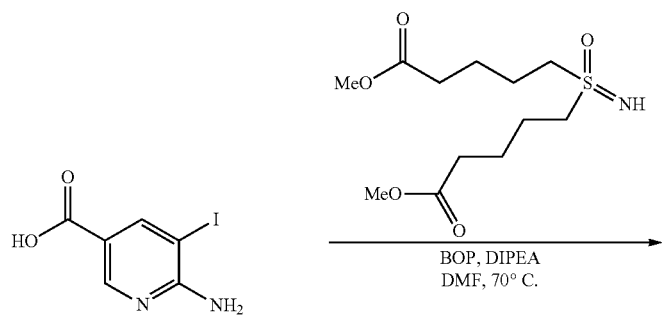

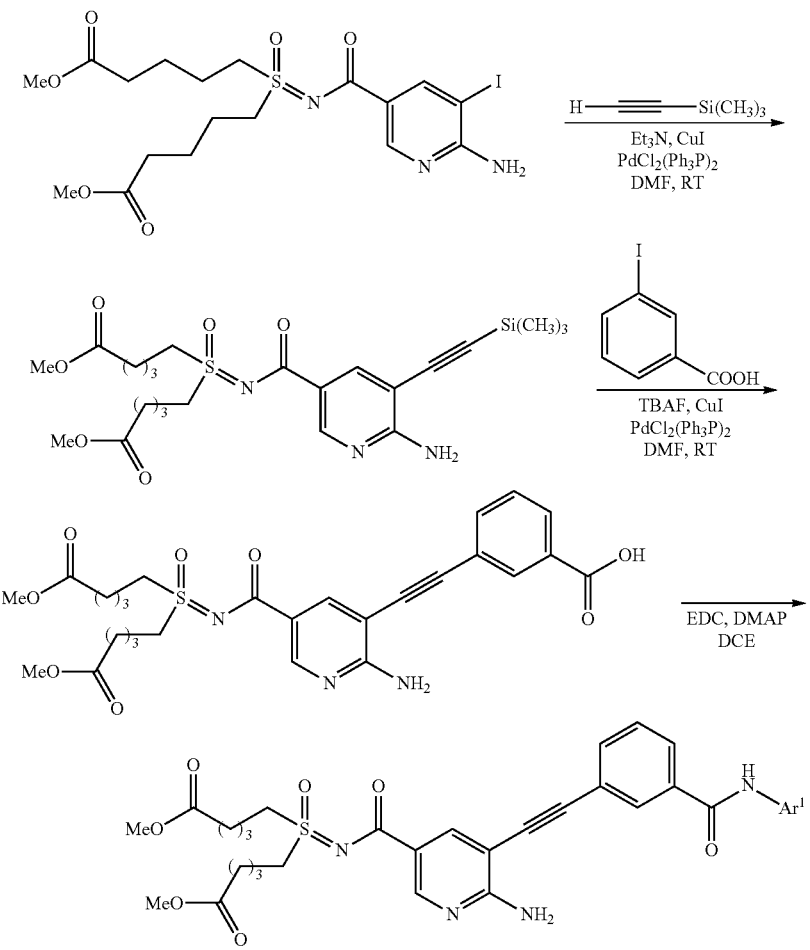
Scheme 4
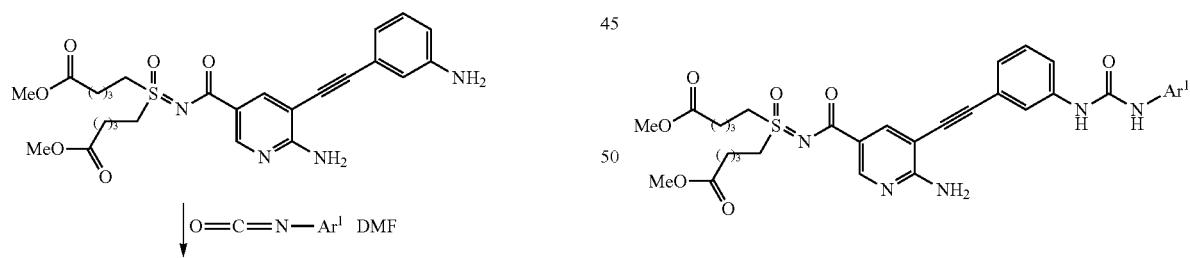
Scheme 5
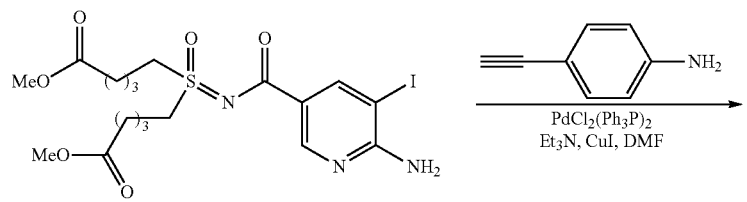

-continued
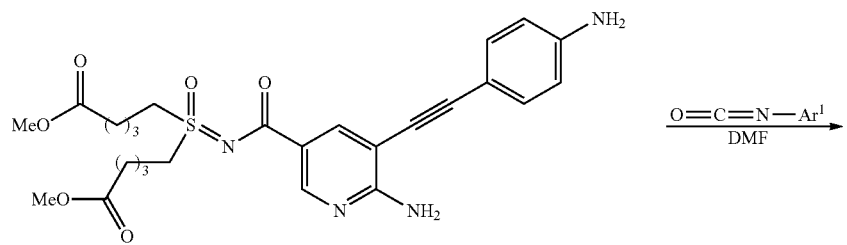
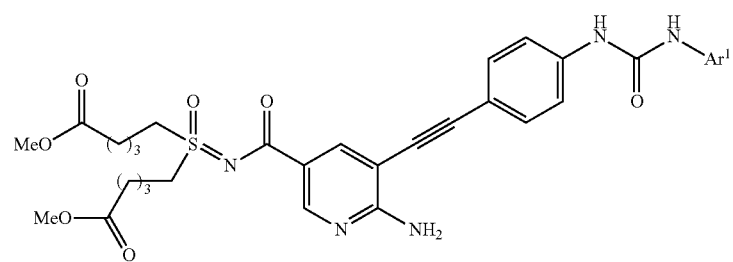
Scheme 6
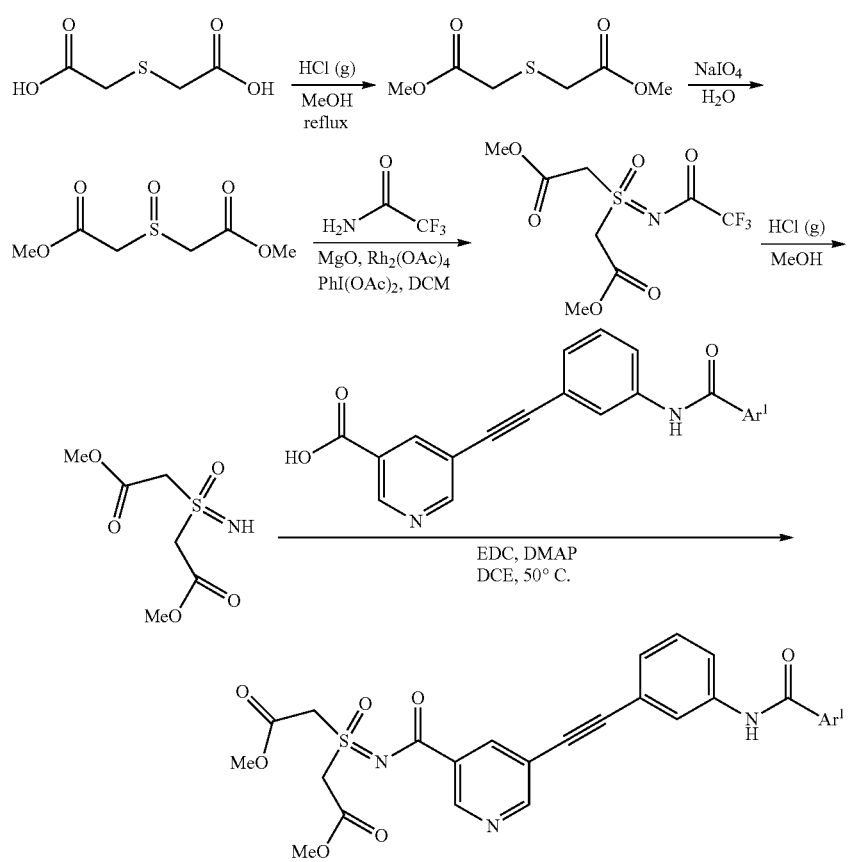

In particular the compounds of the present invention are selected from the compounds of Table 1, below. In Table 1 the compounds of the present invention are exemplified by any combination of $Ar^1$, $R^1$ and $R^2$ attached to the core template illustrated.

TABLE 1

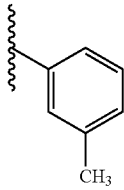

| Example Number | $Ar^1$ | VEGFR2 Kinase (IC$_{50}$, nM) | VEGFR2 Cellular (IC$_{50}$, nM) | PDGFRβ Kinase (IC$_{50}$, nM) | VEGFR1 Kinase (IC$_{50}$, nM) |
|---|---|---|---|---|---|
| 1 | 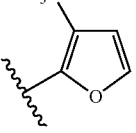 | 9 | <1 | 25 | |
| 2 | 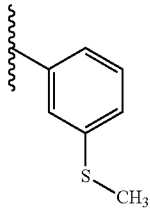 | 3 | 3 | 176 | 10 |
| 3 | 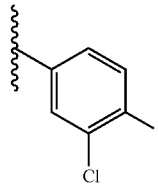 | 5 | 4 | | |
| 4 | 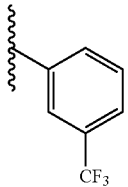 | 8 | 2 | 34 | |
| 5 |  | 10 | 3 | 10 | |

TABLE 1-continued

| Example Number | Ar¹ | VEGFR2 Kinase (IC$_{50}$, nM) | VEGFR2 Cellular (IC$_{50}$, nM) | PDGFRβ Kinase (IC$_{50}$, nM) | VEGFR1 Kinase (IC$_{50}$, nM) |
|---|---|---|---|---|---|
| 6 | 3-Cl-phenyl | 11 | 1 | 21 | |
| 7 | 2-F-5-CH₃-phenyl | 11 | 49 | 29 | 13 |
| 8 | 3-(S(=O)CH₃)-phenyl | 12 | 6 | | |
| 9 | 3-(C(=O)CH₃)-phenyl | 13 | 10 | 81 | |
| 10 | 2-F-5-CF₃-phenyl | 20 | 6 | 69 | |

TABLE 2
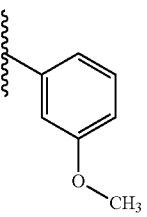
| Example Number | Ar¹ | VEGFR2 Kinase (IC$_{50}$, nM) | VEGFR2 Cellular (IC$_{50}$, nM) | PDGFRβ Kinase (IC$_{50}$, nM) | VEGFR1 Kinase (IC$_{50}$, nM) |
|---|---|---|---|---|---|
| 11 | 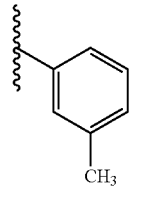 | 4 | 2 | 38 | |
| 12 | 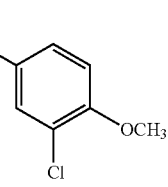 | 8 | 1 | 57 | |
| 13 | 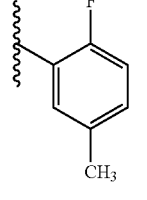 | 9 | 5 | 38 | |
| 14 | 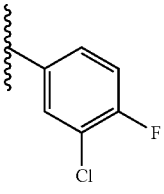 [SMILES: *c1ccc(F)c(Cl)c1] | 11 | <1 | 50 | 14 |
| 15 | 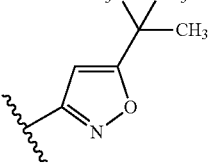 | 15 | 11 | 68 | |
| 16 |  | 28 | | 20 | 27 |

TABLE 2-continued
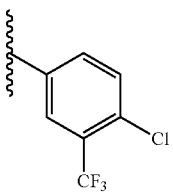 [SMILES: *c1ccc(Cl)c(C(F)(F)F)c1]
| Example Number | Ar¹ | VEGFR2 Kinase (IC$_{50}$, nM) | VEGFR2 Cellular (IC$_{50}$, nM) | PDGFRβ Kinase (IC$_{50}$, nM) | VEGFR1 Kinase (IC$_{50}$, nM) |
|---|---|---|---|---|---|
| 17 | (4-Cl-3-CF₃-phenyl) | 37 | | 36 | 32 |
TABLE 3
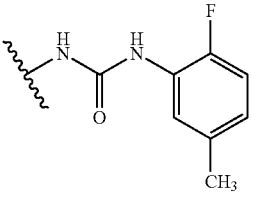
| Example Number | R¹ | R² | VEGFR2 Kinase (IC$_{50}$, nM) | VEGFR2 Cellular (IC$_{50}$, nM) | PDGFRβ Kinase (IC$_{50}$, nM) | VEGFR1 Kinase (IC$_{50}$, nM) |
|---|---|---|---|---|---|---|
| 18 | (urea-2-F-5-CH₃-phenyl) | H | 10 | 23 | | |
| 19 | H | (urea-2-F-5-CH₃-phenyl) | 13 | 5 | 20 | 23 |

TABLE 4

| Example | Structure | VEGFR2 Kinase (IC$_{50}$, nM) | VEGFR2 Cellular (IC$_{50}$, nM) | PDGFRβ Kinase (IC$_{50}$, nM) |
| --- | --- | --- | --- | --- |
| 20 | 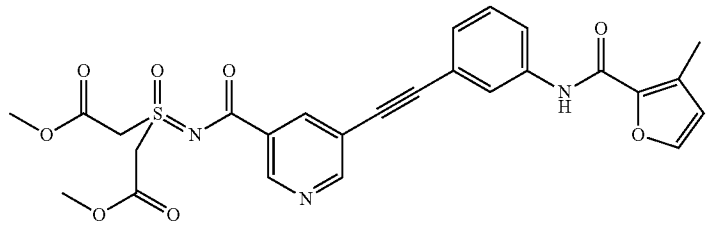 [SMILES: COC(=O)CS(=O)(CC(=O)OC)=NC(=O)c1cncc(C#Cc2cccc(NC(=O)c3occc3C)c2)c1] | 3 | 1 | 62 |
| 21 | 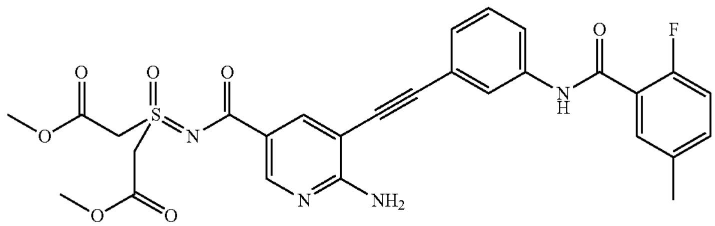 [SMILES: COC(=O)CS(=O)(CC(=O)OC)=NC(=O)c1cnc(N)c(C#Cc2cccc(NC(=O)c3cc(C)ccc3F)c2)c1] | 3 | 1 | 12 |
| 22 | 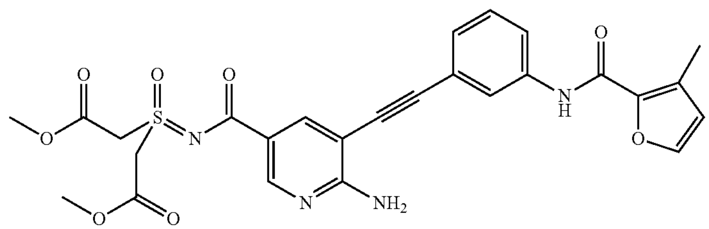 [SMILES: COC(=O)CS(=O)(CC(=O)OC)=NC(=O)c1cnc(N)c(C#Cc2cccc(NC(=O)c3occc3C)c2)c1] | 6 | 175 | 38 |

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenvironment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

Biological data for the compounds of the present invention was generated by use of the following assays.

VEGFR2 Kinase Assay:

Biochemical KDR kinase assays were performed in 96 well microtiter plates that were coated overnight with 75 μg/well of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 A reaction volumes containing 2.7 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain KDR protein (BPS Bioscience, San Diego, Calif.). Following a 15 minute incubation at 30° C., the reactions were washed 2 mls per well PBS-T. 100 μl of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of $2.5NH_2SO_4$ to each well and read using a microplate ELISA reader set at 492 nm. $IC_{50}$ values for compound inhibition were calculated directly from graphs of optical density (arbitrary units) versus compound concentration following subtraction of blank values.

VEGFR2 Cellular Assay

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 384-well fibronectin coated black-walled plates overnight @ 37° C./5% CO2. Cells were loaded with calcium indicator Fluo-4 for 45 minutes at 37° C. Cells were washed 2 times (Elx405, Biotek Instruments) to remove extracellular dye. For screening, cells were pre-incubated with test agents for 30 minutes, at a single concentration (10 uM) or at concentrations ranging from 0.0001 to 10.0 uM followed by $VEGF_{165}$ stimulation (10 ng/mL). Changes in fluorescence at 516 nm were measured simultaneously in all 384 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

PDGFRβ Kinase Assay

Biochemical PDGFRβ kinase assays were performed in 96 well microtiter plates that were coated overnight with 75 μg of poly-Glu-Tyr (4:1) in 10 mM Phosphate Buffered Saline (PBS), pH 7.4. The coated plates were washed with 2 mls per well PBS+0.05% Tween-20 (PBS-T), blocked by incubation with PBS containing 1% BSA, then washed with 2 mls per well PBS-T prior to starting the reaction. Reactions were carried out in 100 μL reaction volumes containing 36 μM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 20 ul per well of kinase buffer containing 200-300 ng purified cytoplasmic domain PDGFR-b protein (Millipore). Following a 60 minute incubation at 30° C., the reactions were washed 2 mls per well PBS-T. 1000 of a monoclonal anti-phosphotyrosine antibody-peroxidase conjugate diluted 1:10,000 in PBS-T was added to the wells for 30 minutes. Following a 2 mls per well wash with PBS-Tween-20, 100 μl of O-Phenylenediamine Dihydrochloride in phosphate-citrate buffer, containing urea hydrogen peroxide, was added to the wells for 7-10 minutes as a colorimetric substrate for the peroxidase. The reaction was terminated by the addition of 100 μl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

The invention is further illustrated by the following non-limiting examples.

EXAMPLE 1

Dimethyl 5,5'-(N-{[6-amino-5-({3-[(3 methylbenzoyl)amino]phenyl}ethynyl) pyridin-3-yl]carbonyl}sulfonimidoyl)dipentanoate Step 1

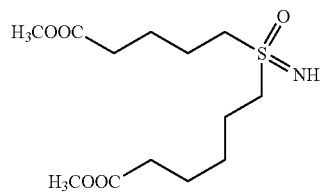

Preparation of Dimethyl 5,5'-sulfonimidoyldipentanoate

Step 1a

Preparation of Methyl 5-bromovalerate

A 2 L 3-neck flask fitted with a mechanical stirrer, condenser, and an argon inlet was charged with 5-bromovaleric acid (103 g, 569 mmol) and MeOH (600 mL). Dimethoxypropane (88.9 g, 853 mmol) was then added followed by conc. $H_2SO_4$ (100 mL) raising the temperature to 45° C. The mixture was refluxed 30 min, then cooled to rt and was left overnight. The mixture was diluted with $H_2O$ (500 mL) and $Et_2O$ (600 mL). The aqueous phase was extracted with $Et_2O$ (2×300 mL). The combined organic phases were then washed with $H_2O$ (400 mL), saturated $NaHCO_3$ (400 mL), $H_2O$ (400 mL), and brine (400 mL). The organic phase was dried over $MgSO_4$ and concentrated to a yellow oil, which stirred under high vacuum to provide an oil (94 g). The oil was then distilled (40-45° C. at 0.3 Torr) to give 92.2 g of methyl 5-bromovalerate at as a colorless liquid (83%).

Step 1b

Preparation of Dimethyl 5,5'-thiadipentanoate

A 1 L 3-neck flask fitted with a stir-bar, condenser, and an argon inlet was charged with methyl 5-bromovalerate (92.0 g, 472 mmol) and MeOH (300 mL). $Na_2S.9H_2O$ (56.7 g, 236 mmol) was added, and the cloudy mixture was heated at reflux for 25 min (If heating was extended the yield lowered).

The mixture was cooled in an ice bath and diluted with half saturated aqueous NaCl (800 mL) and Et$_2$O (200 mL). The aqueous phase was extracted with Et$_2$O (200 mL). The combined organic phases were then washed with 20% aqueous CaCl$_2$ (200 mL) and brine (200 mL). The organic phase was filtered through phase separation paper and concentrated to a light yellow oil, which stirred under high vacuum to give 67.4 g of an oil. The oil was distilled giving an impurity fraction at 54-60° C. at 0.8 Torr with a strong stench. The fraction collected at 140-145° C. at 0.4 Torr gave 31.3 g of dimethyl 5,5'-thiadipentanoate as a light yellow oil (51%). $^1$H NMR (60 MHz, CDCl$_3$): δ 3.6 (s, 6H), 2.6-2.1 (m, 8H), 1.7-1.4 (m, 8H) ppm.

Step 1c

Preparation of Dimethyl 5,5'-sulfinyldipentanoate

A 2 L 3-neck flask fitted with a stir-bar was charged with NaIO$_4$ (26.6 g, 124 mmol) and H$_2$O (300 mL). To the solution was added dimethyl 5,5'-thiadipentanoate (31.1 g, 119 mmol) in MeOH (300 mL). A white precipitate formed after approximately one min. The mixture stirred for 30 min at room temperature and then was diluted with CH$_2$Cl$_2$ (150 mL) and filtered. The solid was rinsed with CH$_2$Cl$_2$ (100 mL). The aqueous phase of the filtrate was extracted with CH$_2$Cl$_2$ (100 mL). The combined organic phases were then washed with H$_2$O (150 mL), filtered through phase separation paper, and concentrated to give 31.8 g of dimethyl5,5'-sulfinyldipentanoate as a yellow solid (96%). $^1$H NMR (60 MHz, CDCl$_3$): δ 3.6 (s, 6H), 2.8-2.5 (m, 4H), 2.5-2.2 (m, 4H), 1.9-1.6 (m, 8H) ppm.

Step 1d

Preparation of Dimethyl 5,5'-sulfonimidoyldipentanoate

A 1 L 3-neck flask fitted with a stir-bar and Ar inlet was charged with trifluoroacetamide (25.8 g, 228 mmol), MgO (18.4 g, 456 mmol), Rh$_2$(OAc)$_2$ (1.00 g, 2.28 mmol), and CH$_2$Cl$_2$ (250 mL). To the turquoise suspension was added dimethyl 5,5t-sulfinyldipentanoate (31.8 g, 114 mmol) and PhI(OAc)$_2$ (55.1 g, 171 mmol) in CH$_2$Cl$_2$ (150 mL) forming a light violet suspension that turned grey with 3 hr of stirring. After 1.5 hr, another 200 mg Rh$_2$(OAc)$_2$ was added, and the mixture stirred overnight. The mixture was filtered through a pad of celite (70 g) and rinsed with CH$_2$Cl$_2$ (500 mL). The filtrate was filtered through a pad of silica gel (150 g) and Na$_2$SO$_4$ (30 g). The silica gel was rinsed with CH$_2$Cl$_2$ (500 mL). The combined filtrates were concentrated to 90 g of a green oil. The oil was stirred with hexanes and decanted (2×350 mL). The tan oil was then stirred under high vacuum to 43 g. MeOH (150 mL) and K$_2$CO$_3$ (47.2 g, 342 mmol) were added, and the mixture stirred 3 hr at rt. H$_2$O (350 mL) and EtOAc (350 mL) were then added. The aqueous phase was next extracted with EtOAc (350 mL). The combined organic phases were washed with brine (250 mL), filtered through phase separation paper, and concentrated to give 29.5 g of a yellow oil. The oil was chromatographed on silica gel (100 g) with a gradient of 1:3 EtOAc:hexanes to 9:1 EtOAc:MeOH. The fractions from 1:1 EtOAc:hexanes to 9:1 EtOAc:MeOH were concentrated to give 22.9 g of dimethyl 5,5'-sulfonimidoyldipentanoate as an amber oil (22.8 g, 69%). $^1$H NMR (300 MHz, CHCl$_3$): δ 4.85 (s, 1H), 3.70 (s, 6H), 3.18-3.08 (m, 4H), 2.44 (t, 4H), 1.92-1.72 (m, 8H) ppm.

Step 2

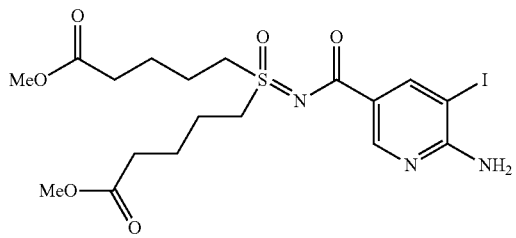 [SMILES: COC(=O)CCCCS(=O)(CCCCC(=O)OC)=NC(=O)c1cnc(N)c(I)c1]

Preparation of Dimethyl 5,5'-{N-[(6-amino-5-iodoppidin-3-yl)carbonyl]sulfonimidoyl}dipentanoate To the reaction solution of amino-iodo-nicotinic acid (1.32 g, 5.0 mmol, 1.0 equiv.), dimethyl5,5'-sulfonimidoyldipentanoate (1.47 g, 5.0 mmol, 1.0 equiv.), and diisopropylethylamine (2.6 mL, 15.0 mmol, 3.0 equiv.) in anhydrous DMF (15 mL) was added BOP (2.43 g, 5.5 mmol, 1.1 equiv.) in one portion under nitrogen atmosphere. The resulting reaction mixture was heated at 70° C. for 1.25 h. The brown reaction solution was cooled to room temperature, diluted with EtOAc, washed sequentially with sat. aq. NaHCO$_3$ (2×), aq. NH$_4$Cl (1×), and brine (1×), and at finally dried with anhydrous Na$_2$SO$_4$. The solution was decanted, concentrated, and the oily residue was subject to a gradient column chromatography (from CHCl$_3$ to MeOH—CHCl$_3$ 1:50) to yield the title compound as reddish oil (1.8 g).

Step 3

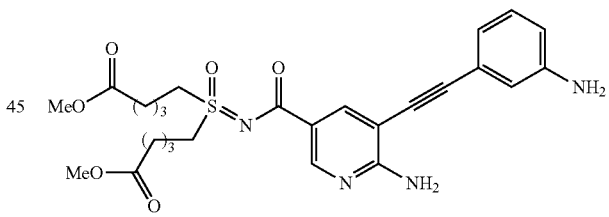

Preparation of Dimethyl 5,5'-[N-({6-amino-5-[(3-aminophenyl)ethynyl]pyridin-3-yl}carbonyl)sulfonimidoyl]dipentanoate To the degassed mixture of dimethyl 5,5'-{N-[(6-amino-5-iodopridin-3-yl)carbonyl]sulfonimidoyl}dipentanoate (1.16 g, 2.15 mmol, 1.0 equiv.), 3-ethynylaniline (0.34 mL, 3.25 mmol, 1.5 equiv.), and triethylamine (1.2 mL, 8.61 mmol, 4.0 equiv.) in anhydrous DMF (7 mL) under nitrogen atmosphere was added CuI (81.5 mg, 0.42 mmol, 0.2 equiv.) and PdCl$_2$(Ph$_3$P)$_2$ (150.6 mg, 0.21 mmol, 0.1 equiv.). The reaction mixture was stirred at room temperature for 15 minutes. The reaction was then diluted with EtOAc, washed with sat. aq. NaHCO$_3$, aq. NH$_4$Cl, and brine, and lastly dried with anhydrous Na$_2$SO$_4$. The solution was decanted, concentrated, and the oily residue was subject to a gradient column chromatography (from EtOAc-Hex 1:3 to neat EtOAc) to give the title compound as a white foam (1.0 g).

Step 4

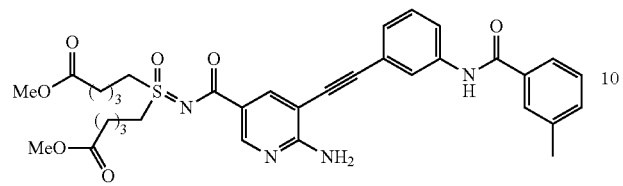

Preparation of Dimethyl 5,5'-(N-{[6-amino-5-({3-[(3-methylbenzoyl)amino]phenyl}ethynyl)pyridin-3-yl]carbonyl}sulfonimidoyl)dipentanoate To the reaction solution of dimethyl 5,5'-[N-({6-amino-5-[(3-aminophenyl)ethynyl]pyridin-3-yl}carbonyl)sulfonimidoyl]dipentanoate (80 mg, 0.15 mmol, 1.0 equiv.), m-toluic acid (60 mg, 0.2 mmol, 1.3 equiv.), and DIPEA (0.11 mL, 0.6 mmol, 4.0 equiv.) in anhydrous DMF (1 mL) was added BOP (120 mg, 0.27 mmol, 1.8 equiv.) under nitrogen atmosphere. The reaction mixture was stirred at room temperature for overnight. It was then diluted with EtOAc, washed with sat. aq. NaHCO$_3$, aq. NH$_4$Cl, and brine, and finally dried with anhydrous Na$_2$SO$_4$. The solution was decanted, concentrated, and the oily residue was subject to a gradient column chromatography (from EtOAc-Hex 1:3 to 4:1) to afford the title compound as clear oil (76 mg). $^1$H NMR (DMSO-d$_6$) δ: 10.29 (s, 1H), 8.57 (d, J=2.1 Hz, 1H), 8.07 (t, J=1.8 Hz, 1H), 8.04 (d, J=2.3 Hz, 1H), 7.79 (s, 1H), 7.74-7.78 (m, 2H), 7.38-7.46 (m, 4H), 7.00 (br. s., 2H), 3.54-3.63 (m, 10H), 2.41 (s, 3H), 2.39 (t, J=7.3 Hz, 4H), 1.71-1.86 (m, 4H), 1.64-1.71 (m, 4H)

In a manner similar to the procedures described for EXAMPLE 1, step 4 the following EXAMPLEs as referenced in Table 1 were prepared.

EXAMPLE 2

Dimethyl 5,5'-(N-{[6-amino-5-({3-[(3-methyl-2-furoyl)amino]phenyl}ethynyl)pyridin-3-yl]carbonyl}sulfonimidoyl)dipentanoate $^1$H NMR (DMSO-d$_6$) δ: 10.13 (s, 1H), 8.56 (d, J=2.1 Hz, 1H), 8.08 (t, J=1.8 Hz, 1H), 8.04 (d, J=2.3 Hz, 1H), 7.81 (d, J=1.5 Hz, 1H), 7.74 (ddd, J=7.6, 1.9, 1.6 Hz, 1H), 7.39-7.43 (m, 1H), 7.35-7.39 (m, 1H), 6.99 (br. s., 2H), 6.60 (d, J=1.5 Hz, 1H), 3.52-3.64 (m, 10H), 2.39 (t, J=15.0 Hz, 4H), 2.35 (s, 3H), 1.71-1.86 (m, 4H), 1.64-1.71 (m, 4H)

EXAMPLE 2A

Dimethyl 5,5'-(N-{[6-amino-5-({3-[(3-methyl-2-furoyl)amino]phenyl}ethynyl)pyridin-3-yl]carbonyl}sulfonimidoyl)diethanoate

EXAMPLE 3

Dimethyl 5,5'-[N-({6-amino-5-[(3-{[3-(methylthio)benzoyl]amino}phenyl)ethynyl]pyridin-3-yl}carbonyl)sulfonimidoyl]dipentanoate $^1$H NMR (DMSO-d$_6$) δ: 10.36 (s, 1H), 8.57 (d, J=2.1 Hz, 1H), 8.05 (t, J=1.8 Hz, 1H), 8.04 (d, J=2.3 Hz, 1H), 7.80-7.82 (m, 1H), 7.76 (dt, J=7.9, 1.6 Hz, 1H), 7.70-7.73 (m, 1H), 7.47-7.51 (m, 2H), 7.43-7.46 (m, 1H), 7.39-7.43 (m, 1H), 7.00 (br. s., 2H), 3.50-3.65 (m, 10H), 2.56 (s, 3H), 2.39 (t, J=7.3 Hz, 4H), 1.71-1.86 (m, 4H), 1.64-1.71 (m, 4H)

EXAMPLE 4

Dimethyl 5,5'-(N-{[6-amino-5-({3-[(3-chloro-4-fluorobenzoyl)amino]phenyl}ethynyl)pyridin-3-yl]carbonyl}sulfonimidoyl)dipentanoate $^1$H NMR (DMSO-d$_6$) δ: 10.43 (s, 1H), 8.57 (d, J=2.1 Hz, 1H), 8.22 (dd, J=7.0, 2.1 Hz, 1H), 8.04 (d, J=2.3 Hz, 2H), 8.01 (ddd, J=8.7, 4.7, 2.2 Hz, 1H), 7.74 (ddd, J=8.1, 1.8, 1.6 Hz, 1H), 7.62 (t, J=9.0 Hz, 1H), 7.45-7.47 (m, 1H), 7.42 (t, J=7.9 Hz, 1H), 7.00 (br. s., 2H), 3.50-3.64 (m, 10H), 2.39 (t, J=7.3 Hz, 4H), 1.71-1.86 (m, 4H), 1.65-1.71 (m, 4H)

EXAMPLE 5

Dimethyl 5,5'-[N-({6-amino-5-[(3-{[3-(trifluoromethyl)benzoyl]amino}phenyl)ethynyl]pyridin-3-yl}carbonyl)sulfonimidoyl]dipentanoate $^1$H NMR (DMSO-d$_6$) δ: 10.56 (s, 1H), 8.57 (d, J=2.3 Hz, 1H), 8.32 (s, 1H), 8.28 (d, J=7.9 Hz, 1H), 8.06 (t, J=1.6 Hz, 1H), 8.04 (d, J=2.3 Hz, 1H), 7.99 (d, J=7.9 Hz, 1H), 7.81 (t, J=7.9 Hz, 1H), 7.78 (dt, J=8.0, 1.6 Hz, 1H), 7.46-7.49 (m, 1H), 7.42-7.45 (m, 1H), 7.01 (br. s., 2H), 3.51-3.65 (m, 10H), 2.39 (d, J=14.7 Hz, 4H), 1.71-1.86 (m, 4H), 1.64-1.71 (m, J=7.3 Hz, 4H)

EXAMPLE 6

Dimethyl 5,5'4N-{[6-amino-5-({3-[(3-chlorobenzoyl)amino]phenyl}ethynyl)pyridin-3-yl]carbonyl}sulfonimidoyl)dipentanoate $^1$H NMR (DMSO-d$_6$) δ: 10.44 (s, 1H), 8.57 (d, J=2.3 Hz, 1H), 8.06 (t, J=1.6 Hz, 1H), 8.04 (d, J=2.1 Hz, 1H), 8.03 (t, J=1.8 Hz, 1H), 7.93 (dt, J=7.8, 0.9 Hz, 1H), 7.75 (dt, J=8.4, 1.5 Hz, 1H), 7.69 (dddd, J=7.8, 1.0, 0.9, 0.6 Hz, 1H), 7.57-7.61 (m, 1H), 7.44-7.48 (m, 1H), 7.40-7.44 (m, 1H), 7.00 (br. s., 2H), 3.50-3.65 (m, 10H), 2.39 (t, J=7.2 Hz, 4H), 1.72-1.86 (m, 4H), 1.64-1.71 (m, 4H)

EXAMPLE 7

Dimethyl 5,5'-(N-{[6-amino-5-({3-[(2-fluoro-5-methylbenzoyl)amino]phenyl}ethynyl)pyridin-3-yl]carbonyl}sulfonimidoyl)dipentanoate $^1$H NMR (DMSO-d$_6$) δ: 10.46 (s, 1H), 8.57 (d, J=2.1 Hz, 1H), 8.04 (d, J=2.3 Hz, 1H), 8.01 (s, 1H), 7.68 (d, J=7.9 Hz, 1H), 7.48 (d, J=6.6, 1.9 Hz, 1H), 7.43-7.46 (m, 1H), 7.36-7.42 (m, 2H), 7.22-7.27 (m, 1H), 7.01 (br. s., 2H), 3.51-3.63 (m, 10H), 2.39 (t, J=7.3 Hz, 4H), 2.34-2.36 (m, 3H), 1.71-1.86 (m, 4H), 1.64-1.70 (m, 4H)

EXAMPLE 8

Dimethyl 5,5'-[N-({6-amino-5-[(3-{[3-(methylsulfinyl)benzoyl]amino}phenyl)ethynyl]pyridin-3-yl}carbonyl)sulfonimidoyl]dipentanoate $^1$H NMR (DMSO-d$_6$) δ: 10.61 (s, 1H), 8.57 (d, J=2.3 Hz, 1H), 8.50 (t, J=1.6 Hz, 1H), 8.29-8.32 (m, 1H), 8.16 (dt, J=7.6, 1.4 Hz, 1H), 8.06 (t, J=1.3 Hz, 1H), 8.04 (d, J=2.3 Hz, 1H), 7.85 (t, J=7.8 Hz, 1H), 7.76-7.79 (m, 1H), 7.42-7.50 (m, 2H), 7.01 (br. s., 2H), 3.51-3.62 (m, 2H), 3.50-3.66 (m, 2H), 3.31 (s, 6H), 3.30 (s, 3H), 2.39 (d, J=14.7 Hz, 4H), 1.63-1.87 (m, 8H)

EXAMPLE 9

Methyl 3-{[(3-{[2-amino-5-({[bis(5-methoxy-5-oxopentyl)(oxido)-lambda~4~-sulfanylidene]amino}carbonyl)pyridin-3-yl]ethynyl}phenyl)amino]carbonyl}benzoate $^1$H NMR (DMSO-d$_6$) δ: 10.56 (s, 1H), 8.57 (d, J=2.3 Hz, 1H), 8.56 (t, J=1.5 Hz, 1H), 8.25 (dt, J=7.8, 1.4 Hz, 1H), 8.18 (ddd, J=7.8, 1.3, 1.2 Hz, 1H), 8.07 (t, J=1.9 Hz, 1H), 8.04 (d, J=2.3 Hz, 1H), 7.78 (dt, J=7.9, 1.6 Hz, 1H), 7.72 (t, J=7.8 Hz, 1H), 7.45-7.48 (m, 1H), 7.40-7.44 (m, 1H), 7.01 (br. s., 2H), 3.91-3.93 (m, 3H), 3.51-3.65 (m, 10H), 2.39 (t, J=7.3 Hz, 4H), 1.72-1.86 (m, 4H), 1.64-1.71 (m, 4H)

EXAMPLE 10

Dimethyl 5,5'-[N-({6-amino-5-[(3-{[2-fluoro-5-(trifluoromethyl)benzoyl]amino}phenyl)ethynyl]pyridin-3-yl}carbonyl)sulfonimidoyl]dipentanoate $^1$H NMR (DMSO-d$_6$) δ: 10.70 (s, 1H), 8.57 (d, J=2.1 Hz, 1H), 8.08 (dd, J=5.1, 1.3 Hz, 1H), 8.04 (d, J=1.8 Hz, 1H), 8.00 (br. s., 2H), 7.61-7.70 (m, 2H), 7.48 (d, J=7.6 Hz, 1H), 7.40-7.45 (m, 1H), 7.02 (br. s., 2H), 3.50-3.63 (m, 10H), 2.39 (t, J=7.2 Hz, 4H), 1.73-1.85 (m, 4H), 1.67 (quin, J=7.2 Hz, 4H)

EXAMPLE 11

Dimethyl 5,5'-[N-({6-amino-5-[(3-{[(3-methoxyphenyl)amino]carbonyl}phenyl)ethynyl]pyridin-3-yl}carbonyl)sulfonimidoyl]dipentanoate Step 1

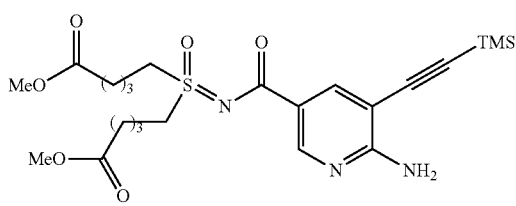

Preparation of Dimethyl 5,5'-[N-({6-amino-5-[(trimethylsilyl)ethynyl]pyridin-3-yl}carbonyl)sulfonimidoyl]dipentanoate To the degassed mixture of dimethyl 5,5'-{N-[(6-amino-5-iodopyridin-3-yl)carbonyl]sulfonimidoyl}dipentanoate (1.8 g, 3.34 mmol, 1.0 equiv.), trimethylsilyacetylene (2.78 mL, 20.0 mmol, 6.0 equiv.), and triethylamine (3.72 mL, 26.7 mmol, 8.0 equiv.) in anhydrous DMF (11 mL) under nitrogen atmosphere was added CuI (127.2 mg, 0.67 mmol, 0.2 equiv.) and PdCl$_2$(Ph$_3$P)$_2$ (234.5 mg, 0.33 mmol, 0.1 equiv.). The reaction mixture was stirred at room temperature for 15 minutes. The reaction was then diluted with EtOAc, washed with sat. aq. NaHCO$_3$, aq. NH$_4$Cl, and brine, and lastly dried with anhydrous Na$_2$SO$_4$. The solution was decanted, concentrated, and the oily residue was subject to a gradient column chromatography (from EtOAc-Hex 1:10 to 4:1) to yield dimethyl 5,5'-[N-({6-amino-5-[(trimethylsilyl)ethynyl]pyridin-3-yl}carbonyl)sulfonimidoyl]dipentartoate as lightly brown oil (1.27 g).

Step 2

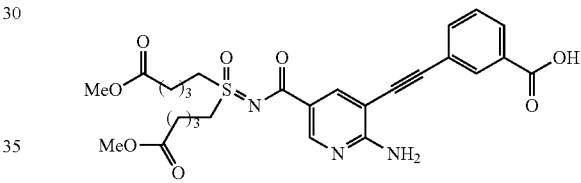

Preparation of 3-{[2-amino-5-({[bis(5-methoxy-5-oxopentyl)(oxido)-λ$^4$-sulfanylidene]amino}carbonyl)pyridin-3-yl]ethynyl}benzoic acid To the degassed mixture of dimethyl 5,5'-[N-({6-amino-5-[(trimethylsilyl)ethynyl]pyridin-3-yl}carbonyl)sulfonimidoyl]dipentanoate (1.27 g, 2.50 mmol, 1.0 equiv.), 3-iodobenzoic acid (0.62 g, 2.5 mmol, 1.0 equiv.), triethylamine (1.39 mL, 10.0 mmol, 4.0 equiv.), and TBAF (2.7 mL, 1.0 M in THF, 1.1 equiv.) in anhydrous DMF (10 mL) under nitrogen atmosphere was added CuI (95.2 mg, 0.5 mmol, 0.2 equiv.) and PdCl$_2$(Ph$_3$P)$_2$ (175 mg, 0.25 mmol, 0.1 equiv.). The reaction mixture was stirred at room temperature for 15 minutes. The reaction was then diluted with EtOAc and washed with aq. NH$_4$Cl. The aqueous layer was extracted once with i-PrOH—CHCl$_3$ (1:5) and all organic layers were combined. The combined organic layer was then washed with brine and dried with anhydrous Na$_2$SO$_4$. The solution was decanted, concentrated, and the oily residue was twice subject to a gradient column chromatography (from CHCl$_3$ to MeOH 1:9 and from CH$_2$Cl$_2$ to MeOH—CH$_2$Cl$_2$ 1:9) to yield 3-{[2-amino-5-({[bis(5-methoxy-5-oxopentyl)(oxido)-λ$^4$-sulfanylidene]amino}carbonyl)pyridin-3-yl]ethynyl}benzoic acid as a yellow solid (0.85 g).

Step 3

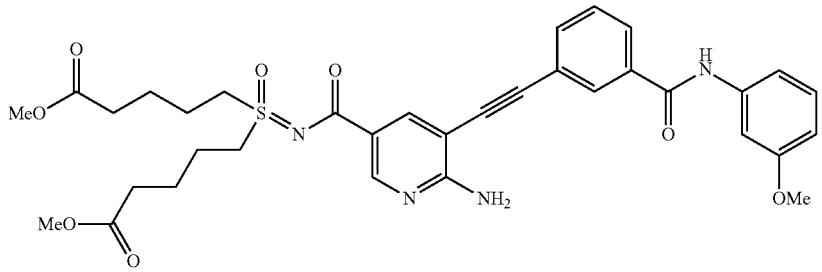 [SMILES: COC(=O)CCCCS(=O)(CCCCC(=O)OC)=NC(=O)c1cnc(N)c(C#Cc2cccc(C(=O)Nc3cccc(OC)c3)c2)c1]

Preparation of dimethyl 5,5'-[N-({6-amino-5-[(3-{[(3 methoxyphenyl)amino]carbonyl}phenyl)ethynyl]pyridin-3-yl}carbonyl)sulfonimidoyl]dipentanoate The reaction mixture of 3-{[2-amino-5-({[bis(5-methoxy-5-oxopentyl)(oxido)-sulfanylidene]amino}carbonyl)pyridin-3-yl]ethynyl}benzoic acid (56 mg, 0.1 mmol, 1.0 equiv.), m-anisidine (13.4 μL, 0.12 mmol, 1.2 equiv.), DMAP (2.5 mg, 0.02 mmol, 0.2 equiv.) and EDC (29 mg, 0.15 mmol, 1.5 equiv.) in DCE (1 mL) in a sealed vial was stirred and heated at 60° C. for 3 hours. The resulting brown solution was diluted with EtOAc, washed with sat. aq. NaHCO$_3$, aq. NH$_4$Cl, and brine, and finally dried with anhydrous Na$_2$SO$_4$. The solution was decanted, concentrated, and the oily residue was subject to a gradient column chromatography (from EtOAc-Hex 1:4 to 6:1) to yield Dimethyl 5,5'-[N-({6-amino-5-[(3-{[(3-methoxyphenyl)amino]carbonyl}phenyl)ethynyl]pyridin-3-yl}carbonyl)sulfonimidoyl]dipentanoate as clear oil (28 mg). $^1$H NMR (DMSO-d$_6$) δ: 10.30 (s, 1H), 8.58 (d, J=2.1 Hz, 1H), 8.26 (t, J=1.5 Hz, 1H), 8.07 (s, 1H), 7.93 (dt, J=7.8, 1.7 Hz, 1H), 7.89 (dt, J=7.8, 1.1 Hz, 1H), 7.58 (d, J=15.6 Hz, 1H), 7.47 (t, J=2.2 Hz, 1H), 7.39 (dd, J=7.9, 0.9 Hz, 1H), 7.26 (t, J=8.2 Hz, 1H), 7.10 (br. s., 2H), 6.70 (dd, J=8.2, 1.8 Hz, 1H), 3.76 (s, 3H), 3.52-3.63 (m, 10H), 2.39 (d, J=14.7 Hz, 4H), 1.73-1.85 (m, 4H), 1.65-1.71 (m, 4H)

In a manner similar to that described for the preparation of EXAMPLE 11, step 3 the following compounds as shown in Table 2 were prepared

EXAMPLE 12

Dimethyl 5,5'-[N-({6-amino-5-[(3-{[(3-methylphenyl)amino]carbonyl}phenyl)ethynyl]pyridin-3-yl}carbonyl)sulfonimidoyl]dipentanoate $^1$H NMR (DMSO-d$_6$) δ: 10.25 (s, 1H), 8.58 (d, J=2.3 Hz, 1H), 8.26 (t, J=1.5 Hz, 1H), 8.07 (d, J=2.1 Hz, 1H), 7.93 (ddd, J=7.8, 1.5, 1.3 Hz, 1H), 7.89 (dt, J=7.6, 1.2 Hz, 1H), 7.62 (s, 1H), 7.58 (t, J=6.9 Hz, 1H), 7.58 (d, J=7.9 Hz, 1H), 7.24 (t, J=7.9 Hz, 1H), 7.09 (br. s., 2H), 6.94 (d, J=7.3 Hz, 1H), 3.50-3.65 (m, 10H), 2.39 (t, J=7.3 Hz, 4H), 2.31-2.32 (m, 3H), 1.72-1.87 (m, 4H), 1.64-1.71 (m, 4H)

EXAMPLE 13

Dimethyl 5,5'-[N-({6-amino-5-[(3-{[(3-chloro-4-methoxyphenyl)amino]carbonyl}phenyl)ethynyl]pyridin-3-yl}carbonyl)sulfonimidoyl]dipentanoate $^1$H NMR (DMSO-d$_6$) δ: 10.33 (s, 1H), 8.58 (d, J=2.1 Hz, 1H), 8.25 (s, 1H), 8.07 (d, J=2.3 Hz, 1H), 7.91-7.96 (m, 2H), 7.89 (d, J=7.9 Hz, 1H), 7.69 (dd, J=9.1, 2.6 Hz, 1H), 7.58 (t, J=7.6 Hz, 1H), 7.17 (d, J=9.1 Hz, 1H), 7.09 (br. s., 2H), 3.83-3.86 (m, 3H), 3.52-3.64 (m, 10H), 2.39 (t, J=7.2 Hz, 4H), 1.71-1.86 (m, 4H), 1.63-1.71 (m, 4H)

EXAMPLE 14

Dimethyl 5,5'-[N-({6-amino-5-[(3-{[(2-fluoro-5-methylphenyl)amino]carbonyl}phenyl)ethynyl]pyridin-3-yl}carbonyl)sulfonimidoyl]dipentanoate $^1$H NMR (DMSO-d$_6$) δ: 10.14 (s, 1H), 8.58 (d, J=2.3 Hz, 1H), 8.27 (s, 1H), 8.07 (d, J=2.1 Hz, 1H), 7.95 (d, J=7.9 Hz, 1H), 7.90 (d, J=7.6 Hz, 1H), 7.58 (t, J=7.8 Hz, 1H), 7.41 (d, J=7.3 Hz, 1H), 7.18 (dd, J=10.3, 8.5 Hz, 1H), 7.05-7.11 (m, 3H), 3.51-3.64 (m, 10H), 2.39 (t, J=7.3 Hz, 4H), 2.31 (s, 3H), 1.72-1.85 (m, 4H), 1.64-1.71 (m, 4H)

EXAMPLE 15

Dimethyl 5,5'-[N-({6-amino-5-[(3-{[(3-chloro-4-fluorophenyl)amino]carbonyl}phenyl)ethynyl]pyridin-3-yl}carbonyl)sulfonimidoyl]dipentanoate $^1$H NMR (DMSO-d$_6$) δ: 10.52 (s, 1H), 8.58 (d, J=2.1 Hz, 1H), 8.26 (t, J=1.8 Hz, 1H), 8.09 (dd, J=7.0, 2.6 Hz, 1H), 8.07 (d, J=2.1 Hz, 1H), 7.94 (dt, J=7.7, 1.4 Hz, 1H), 7.91 (ddd, J=7.8, 1.2, 1.0 Hz, 1H), 7.74 (ddd, J=9.0, 4.2, 2.6 Hz, 1H), 7.60 (t, J=7.8 Hz, 1H), 7.44 (t, J=9.1 Hz, 1H), 7.10 (br. s., 2H), 3.51-3.65 (m, 10H), 2.39 (t, J=7.2 Hz, 4H), 1.72-1.86 (m, J=9.7 Hz, 4H), 1.63-1.72 (m, 4H)

EXAMPLE 16

Dimethyl 5,5'-[N-({6-amino-5-[(3-{[(5-tert-butyl-isoxazol-3-yl)amino]carbonyl}phenyl)ethynyl]pyridin-3-yl}carbonyl)sulfonimidoyl]dipentanoate $^1$H NMR (DMSO-d$_6$) δ: 11.40 (s, 1H), 8.58 (d, J=2.3 Hz, 1H), 8.31 (t, J=1.5 Hz, 1H), 8.07 (d, J=2.1 Hz, 1H), 7.99 (dt, J=7.9, 1.3 Hz, 1H), 7.91 (ddd, J=7.8, 1.6, 1.5 Hz, 1H), 7.58 (t, J=7.8 Hz, 1H), 7.08 (br. s., 2H), 6.72-6.74 (m, 1H), 3.52-3.64 (m, 10H), 2.39 (d, J=14.7 Hz, 4H), 1.71-1.86 (m, 4H), 1.65-1.71 (m, 4H), 1.33 (s, 9H)

EXAMPLE 17

Dimethyl 5,5'-{N-[(6-amino-5-{[3-({[4-chloro-3-(trifluoromethyl)phenyl]amino}carbonyl)phenyl]ethynyl}pyridin-3-yl)carbonyl]sulfonimidoyl}dipentanoate $^1$H NMR (DMSO-d$_6$) δ: 10.72-10.74 (m, 1H), 8.58 (d, J=2.3 Hz, 1H), 8.37 (d, J=2.6 Hz, 1H), 8.29 (t, J=1.5 Hz, 1H), 8.14 (dd, J=8.8, 2.6 Hz, 1H), 8.07 (d, J=2.3 Hz, 1H), 7.96 (dt, J=7.9, 1.5 Hz, 1H), 7.93 (ddd, J=7.8, 1.3, 1.2 Hz, 1H), 7.74 (d, J=8.8 Hz, 1H), 7.61 (t, J=7.8 Hz, 1H), 7.10 (br. s., 2H), 3.51-3.64 (m, 10H), 2.39 (t, J=7.3 Hz, 4H), 1.72-1.85 (m, 4H), 1.65-1.71 (m, 4H)

EXAMPLE 18

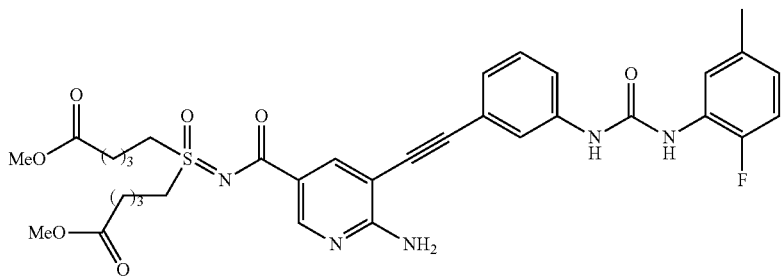

Dimethyl 5,5'-{N-[(6-amino-5-{[3-({[(2-fluoro-5-methylphenyl)amino]carbonyl}amino)phenyl]ethynyl}pyridin-3-yl)carbonyl]sulfonimidoyl}dipentanoate The reaction solution of dimethyl 5,5'-[N-({6-amino-5-[(3-aminophenyl)ethynyl]pyridin-3-yl}carbonyl)sulfonimidoyl]dipentanoate (140 mg, 0.265 mmol, 1.0 equiv.) and 2-fluoro-5-methylphenyl isocyanate (38.8 μL, 0.292 mmol, 1.1 equiv.) in DMF (3 mL) was stirred at room temperature for 3 hours. It was then diluted with EtOAc, washed with sat. aq. NaHCO$_3$, aq. NH$_4$Cl, and brine, and finally dried with anhydrous Na$_2$SO$_4$. The solution was decanted, concentrated, and the oily residue was subject to a gradient column chromatography (from EtOAc-Hex 1:5 to 5:1) yielding the title compound as clear oil (169 mg). $^1$H NMR (DMSO-d$_6$) δ: 9.14-9.15 (m, 1H), 8.56 (d, J=2.3 Hz, 1H), 8.54 (d, J=2.3 Hz, 1H), 8.04 (d, J=2.1 Hz, 1H), 7.99 (dd, J=7.9, 1.8 Hz, 1H), 7.81 (t, J=–1.8 Hz, 1H), 7.40 (dt, J=7.7, 1.9 Hz, 1H), 7.30-7.35 (m, 2H), 7.11 (dd, J=11.3, 8.4 Hz, 1H), 7.00 (br. s., 2H), 6.79-6.83 (m, 1H), 3.52-3.64 (m, 10H), 2.39 (t, J=7.3 Hz, 4H), 2.27 (s, 3H), 1.72-1.85 (m, 4H), 1.65-1.71 (m, 4H)

EXAMPLE 19

Dimethyl 5,5'-{N-[(6-amino-5-{[4-({[(2-fluoro-5-methylphenyl)amino]carbonyl}amino)phenyl]ethynyl}pyridin-3-yl)carbonyl]sulfonimidoyl}dipentanoate Step 1

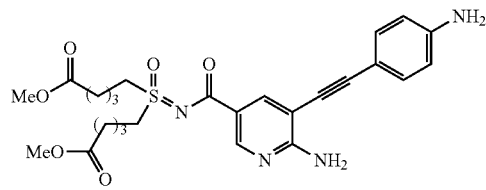

Preparation of dimethyl 5,5'-[N-({6-amino-5-[(4-aminophenyl)ethynyl]pyridin-3-yl}carbonyl)sulfonimidoyl]dipentanoate To the degassed mixture of dimethyl 5,5'-{N-[(6-amino-5-iodopyridin-3-yl)carbonyl]sulfonimidoyl}dipentanoate (234 mg, 0.434 mmol, 1.0 equiv.), 4-ethynylaniline (76.3 mg, 0.651 mmol, 1.5 equiv.), and triethylamine (0.242 mL, 1.736 mmol, 4.0 equiv.) in anhydrous DMF (2 mL) under nitrogen atmosphere was added CuI (16.5 mg, 0.087 mmol, 0.2 equiv.) and PdCl$_2$(Ph$_3$P)$_2$ (30.5 mg, 0.043 mmol, 0.1 equiv.). The reaction mixture was stirred at room temperature for 15 minutes. The reaction was then diluted with EtOAc, washed with sat. aq. NaHCO$_3$, aq. NH$_4$Cl, and brine, and lastly dried with anhydrous Na$_2$SO$_4$. The solution was decanted, concentrated, and the oily residue was subject to a gradient column chromatography (from EtOAc-Hex 1:3 to EtOAc) yielding dimethyl 5,5'-[N-({6-amino-5-[(4-aminophenyl)ethynyl]pyridin-3-yl}carbonyl)sulfonimidoyl]dipentanoate as brown oil (220 mg).

Step 2

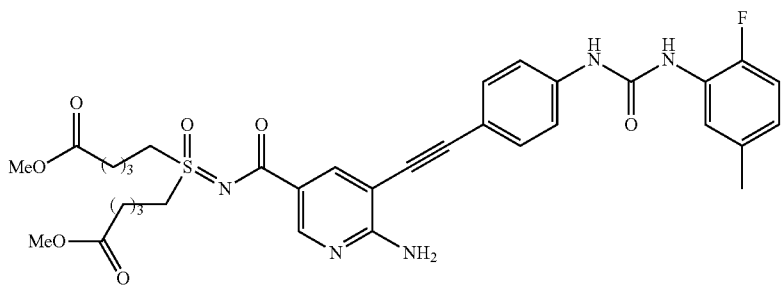

Preparation of dimethyl 5,5'-{N-[(6-amino-5-{[3-({[(2-fluoro-5-methylphenyl)amino]carbonyl}amino)phenyl]ethynyl}pyridin-3-yl)carbonyl]sulfonimidoyl}dipentanoate The reaction solution of 5,5'-[N-({6-amino-5-[(4-aminophenyl)ethynyl]pyridin-3-yl}carbonyl)sulfonimidoyl]dipentanoate (140 mg, 0.265 mmol, 1.0 equiv.) and 2-fluoro-5-methylphenyl isocyanate (38.8 μL, 0.292 mmol, 1.1 equiv.) in DMF (3 mL) was stirred at room temperature for 3 hours. It was then diluted with EtOAc, washed with sat. aq. NaHCO₃, aq. NH₄Cl, and brine, and finally dried with anhydrous Na₂SO₄. The solution was decanted, concentrated, and the oily residue was subject to a gradient column chromatography (from EtOAc-Hex 1:4 to EtOAc) yielding dimethyl 5,5'-{N-[(6-amino-5-{[3-({[(2-fluoro-5-methylphenyl)amino]carbonyl}amino)phenyl]ethynyl}pyridin-3-yl)carbonyl]sulfonimidoyl}dipentanoate as lightly yellow foam (89 mg). $^1$H NMR (DMSO-d$_6$) δ: 9.26 (s, 1H), 8.53-8.55 (m, 2H), 8.00 (d, J=2.1 Hz, 1H), 7.97 (d, J=7.6 Hz, 1H), 7.61 (d, J=8.5 Hz, 2H), 7.49 (s, 2H), 7.11 (dd, J=11.3, 8.4 Hz, 1H), 6.91-6.99 (m, 2H), 6.80-6.84 (m, 1H), 3.51-3.64 (m, 10H), 2.39 (t, J=7.2 Hz, 4H), 2.28 (s, 3H), 1.72-1.85 (m, 4H), 1.65-1.71 (m, 4H)

EXAMPLE 20

Dimethyl 5,5'-(N-{[6-amino-5-({3-[(3-methyl-2-furoyl)amino]phenyl}ethynyl)pyridin-3-yl]carbonyl}sulfonimidoyl)diethanoate Step 1

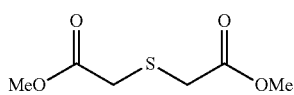 [SMILES: COC(=O)CSCC(=O)OC]

Preparation of Dimethyl 2,2'-thiodiacetate

To 300 mL anhydrous methanol in a 350 mL high pressure bottle was bubbled a stream of gaseous hydrogen chloride for about 10 minutes. Thiodiacetic acid (4 g, 26.7 mmol) was then added and the bottle was sealed and heated at 80° C. overnight. The reaction solution was then concentrated under reduced pressure to give dimethyl 2,2'-thiodiacetate as clear oil (4.54 g).

Step 2

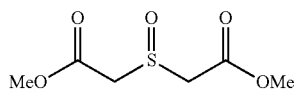 [SMILES: COC(=O)CS(=O)CC(=O)OC]

Preparation of Dimethyl 2,2'-sulfinyldiacetate

To the mixture of dimethyl 2,2'-thiodiacetate (4.54 g, 25.5 mmol, 1 eq) in water (50 mL) at 0° C. was added sodium (meta)periodate (5.786 g, 1.05 eq) and the resulting reaction mixture was stirred overnight. The mixture was then diluted with brine and extracted with CHCl₃ (5×). All organics were combined and dried with anhydrous sodium sulfate. The solution was decanted, concentrated under reduced pressure, and the clear oily residue was subject to column chromatography (EtOAc-Hex 1:5 to 1:1) giving dimethyl 2,2'-sulfinyldiacetate as a clear oil (4.522 g).

Step 3

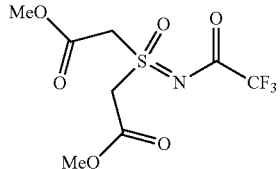 [SMILES: COC(=O)CS(=O)(CC(=O)OC)=NC(=O)C(F)(F)F]

Preparation of dimethyl 2,2'-[N-(trifluoroacetyl)sulfonimidoyl]diacetate

Trifluoroacetamide (5.43 g, 2 eq), magnesium oxide (3.756 g, 4 eq), and rhodium(II) acetate dimer (309 mg, 0.03 eq) were placed in a 500 mL round-bottom flask. Dichloromethane (230 mL) was added followed by dimethyl 2,2'-sulfinyldiacetate (4.52 g, 23.3 mmol, 1 eq), followed by addition of diacetoxyiodobenzene in small portions (11.257 g, 1.5 eq). The mixture was stirred at room temperature for 7 hours. Following that, an additional 2.2 g of trifluoroacetamide was added followed by the addition of additional amount of rhodium(II) acetate dimer (~150 mg) and diacetoxyiodobenzene (3.0 g). The reaction mixture was stirred further at room temperature overnight. The mixture was then filtered through a pad of celite and the pad was washed with MeOH—CHCl₃ (1:5). The filtrate was concentrated and the oily residue was subject to column chromatography twice (from hexane to EtOAc-Hex 1:1) yielding dimethyl 2,2'-[N-(trifluoroacetyl) sulfonimidoyl]diacetate as a brown oil (7.0 g).

Step 4

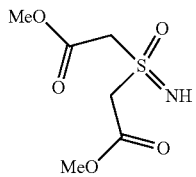

Preparation of dimethyl 2,2'-sulfonimidoyldiacetate

To the reaction vessel containing dimethyl 2,2'[N-(trifluoroacetyl)sulfonimidoyl]diacetate (2 g, 6.56 mmol) was added hydrogen chloride in methanol (1.25 M) (50 mL) and the vessel was sealed and stirred at room temperature for an overnight. The reaction solution was then concentrated and the white solid residue was subject to chromatography (EtOAc-hex 1:9 to 1:1) yielding dimethyl2,2'-sulfonimidoyldiacetate as a slightly brown oil (608 mg).

Step 5

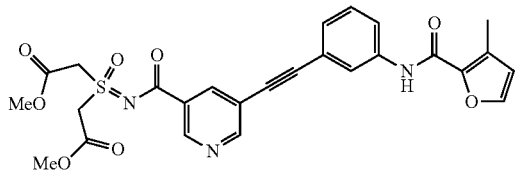 [SMILES: COC(=O)CS(=O)(CC(=O)OC)=NC(=O)c1cncc(C#Cc2cccc(NC(=O)c3occc3C)c2)c1]

Preparation of dimethyl 2,2'-(N-{[5-({3-[(3-methyl-2-furoyl)amino]phenyl}ethynyl)pyridin-3-yl] carbonyl}sulfonimidoyl)diacetate To the mixture of 5-{3-[(3-Methyl-furan-2-carbonyl)-amino]-phenylethynyl}-nicotinic acid (173 mg, 0.5 mmol, 1 eq), EDC (144 mg, 1.5 eq), and DMAP (12.2 mg, 0.2 eq) in DCE (5 mL) was added the dimethyl 2,2'-sulfonimidoyldiacetate (104.5 mg, 1 eq). After the reaction mixture was stirred and heated at 50° C. for 1 hour, it was cooled to room temperature and partitioned between EtOAc and aq NH₄Cl. The organic layer was isolated, washed with brine once, and finally dried with anhydrous sodium sulfate. The solution was decanted, concentrated, and the oily residue was subject to column chromatography (EtOAc-Hex 1:25 to 1:2). The fractions containing the desired product was collected, concentrated, and the white solid that crashed-out was filtered giving dimethyl {[5-({3-[(3-methyl-2-furoyl)amino] phenyl}ethynyl)pyridin-3-yl]carbonyl}sulfonimidoyl)diacetate as white solid in amount of 179 mg.

¹H NMR (DMSO-d₆) δ: 10.21 (s, 1H), 9.04 (d, J=2.1 Hz, 1H), 8.95 (d, J=2.1 Hz, 1H), 8.34 (t, J=2.1 Hz, 1H), 8.14 (t, J=2.2 Hz, 1H), 7.82 (s, 1H), 7.78-7.81 (m, 1H), 7.41 (t, J=7.9 Hz, 1H), 7.34 (dt, J=7.6, 1.3 Hz, 1H), 6.61 (d, J=1.5 Hz, 1H), 4.98-5.11 (m, 4H), 3.76 (s, 6H), 2.35 (s, 3H)

In a manner similar to the procedures described for EXAMPLE 20, step 5 the following EXAMPLEs as referenced in Table 4 were prepared.

EXAMPLE 21

Dimethyl 5,5'-[N-({6-amino-5-[(3-{[(3-chloro-4-fluorophenyl)amino]carbonyl}phenyl)ethynyl]pyridin-3-yl}carbonyl)sulfonimidoyl]diethanoate

EXAMPLE 22

Dimethyl 5,5'-(N-{[6-amino-5-({3-[(3 methylbenzoyl)amino]phenyl}ethynyl)pyridin-3-yl] carbonyl}sulfonimidoyl)diethanoate The present invention is not to be limited in scope by the exemplified embodiments which are intended as illustrations of single aspects of the invention only. Indeed, various modifications of the invention in addition to those described herein will become apparent to those skilled in the art from the foregoing description.

For example, the novel compounds of this invention include any compound which is a 2 and/or 6 amino, 5 arylethynyl, e.g. a phenylethynyl, 3 carbonylsulfonimidoyl pyridine, wherein said arylethynyl, e.g. said phenylethynyl is substituted with an aryl group and binds to the tyrosine kinase receptor.

Preferably, said sulfonylimidoyl is a dialkanoate ester. e.g. a dialkyl alkanoate ester such as dimethyl dipentanoate, and said aryl substituent is linked to said arylethynyl group by a linking group represented by the formula —(NH)$_p$—C(O)—(NH)— wherein p is 0 or 1 and q is 0 or 1. More preferably, said aryl substituent is selected from the group consisting of phenyl and furanyl.

These compounds may be prepared and tested for tyrosine kinase inhibiting activity by the preparatory methods and assays disclosed above.

Such modifications are intended to fall within the scope of the appended claims.

All references cited herein are hereby incorporated by reference in their entirety. Also, the compounds of the present invention may be tested by the various in-vitro and in-vivo assays disclosed in such references to demonstrate the claimed utilities.

What is claimed is:
1. A compound represented by the general formula I

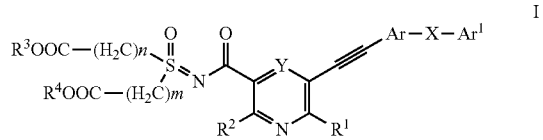

wherein:
R¹ is hydrogen or NH₂;
R² is hydrogen or NH₂;

X is selected from the group consisting of

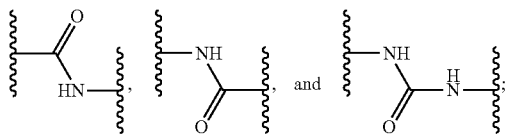

Y is CH or N;
Ar is an aryl group, wherein said aryl group may be optionally substituted with halogen, alkyl, alkoxy, or alkoxycarbonyl;
$Ar^1$ is an aryl group, wherein said aryl group may be optionally substituted with halogen, alkyl, alkoxy, alkoxycarbonyl, sulfinyl, thioether, fluoro or chloro-substituted lower alkyl;
$R^3$ is hydrogen or lower alkyl;
$R^4$ is hydrogen or lower alkyl;
n is an integer of from 1 to 6; and
m is an integer of from 1 to 6; or a pharmaceutically acceptable salt of said compound.

2. The compound of claim 1 wherein Y is CH.
3. The compound of claim 2 wherein Ar is phenyl.
4. The compound of claim 3 wherein $R^1$ is $NH_2$.
5. The compound of claim 4 wherein $R^2$ is hydrogen.
6. The compound of claim 5 wherein $R^3$ is methyl.
7. The compound of claim 6 wherein $R^4$ is methyl.
8. The compound of claim 7 wherein n is an integer of 1 or 4.
9. The compound of claim 8 wherein m is an integer of 1 or 4.
10. The compound of claim 9 wherein $Ar^1$ is selected from the group consisting of phenyl, furanyl and pyrrolyl, which is substituted with fluoro, chloro, lower alkyl, lower alkoxy, loweralkoxycarbonyl, lower alkylsulfinyl, lower alkylthioether, fluoro-substituted lower alkyl or chloro-substituted lower alkyl.
11. The compound of claim 10 wherein the substituent is selected from the group consisting of methyl, tertiary butyl, fluoro, chloro, trifluoromethyl, methoxy, methylsulfinyl, methylthioether and methoxycarbonyl.
12. A compound of selected from the group consisting of
Dimethyl 5,5'-(N-{[6-amino-5-({3-[(3-methylbenzoyl)amino]phenyl}ethynyl)pyridin-3-yl]carbonyl}sulfonimidoyl)dipentanoate,
Dimethyl 5,5'-(N-{[6-amino-5-({3-[(3-methyl-2-furoyl)amino]phenyl}ethynyl)pyridin-3-yl]carbonyl}sulfonimidoyl)dipentanoate,
Dimethyl 5,5'-[N-({6-amino-5-[(3-{[3-(methylthio)benzoyl]amino}phenyl)ethynyl]pyridin-3-yl}carbonyl)sulfonimidoyl]dipentanoate,
Dimethyl 5,5'-(N-{[6-amino-5-({3-[(3-chloro-4-fluorobenzoyl)amino]phenyl}ethynyl)pyridin-3-yl]carbonyl)sulfonimidoyl)dipentanoate,
Dimethyl 5,5'-[N-({6-amino-5-[(3-{[3-(trifluoromethyl)benzoyl]amino}phenyl)ethynyl]pyridin-3-yl}carbonyl)sulfonimidoyl]dipentanoate,
Dimethyl 5,5'-(N-{[6-amino-5-({3-[(3-chlorobenzoyl)amino]phenyl}ethynyl)pyridin-3-yl]carbonyl}sulfonimidoyl)dipentanoate,
Dimethyl 5,5'-(N-{[6-amino-5-({3-[(2-fluoro-5-methylbenzoyl)amino]phenyl}ethynyl)pyridin-3-yl]carbonyl}sulfonimidoyl)dipentanoate,
Dimethyl 5,5'-[N-({6-amino-5-[(3-{[3-(methylsulfinyl)benzoyl]amino}phenyl)ethynyl]pyridin-3-yl}carbonyl)sulfonimidoyl]dipentanoate,
Methyl 3-{[(3-{[2-amino-5-({[bis(5-methoxy-5-oxopentyl)(oxido)-$\lambda^4$-sulfanylidene]amino}carbonyl)pyridin-3-yl]ethynyl}phenyl)amino]carbonyl}benzoate,
Dimethyl 5,5'-[N-({6-amino-5-[(3-{[2-fluoro-5-(trifluoromethyl)benzoyl]amino}phenyl)ethynyl]pyridin-3-yl}carbonyl)sulfonimidoyl]dipentanoate,
Dimethyl 5,5'-[N-({6-amino-5-[(3-{[(3-methoxyphenyl)amino]carbonyl}phenyl)ethynyl]pyridin-3-yl}carbonyl)sulfonimidoyl]dipentanoate,
Dimethyl 5,5'-[N-({6-amino-5-[(3-{[(3-methylphenyl)amino]carbonyl}phenyl)ethynyl]pyridin-3-yl}carbonyl)sulfonimidoyl]dipentanoate,
Dimethyl 5,5'-[N-({6-amino-5-[(3-{[(3-chloro-4-methoxyphenyl)amino]carbonyl}phenyl)ethynyl]pyridin-3-yl}carbonyl)sulfonimidoyl]dipentanoate,
Dimethyl 5,5'-[N-({6-amino-5-[(3-{[(2-fluoro-5-methylphenyl)amino]carbonyl}phenyl)ethynyl]pyridin-3-yl}carbonyl)sulfonimidoyl]dipentanoate,
Dimethyl 5,5'-[N-({6-amino-5-[(3-{[(3-chloro-4-fluorophenyl)amino]carbonyl}phenyl)ethynyl]pyridin-3-yl}carbonyl)sulfonimidoyl]dipentanoate,
Dimethyl 5,5'-[N-({6-amino-5-[(3-{[(5-tert-butylisoxazol-3-yl)amino]carbonyl}phenyl)ethynyl]pyridin-3-yl}carbonyl)sulfonimidoyl]dipentanoate,
Dimethyl 5,5'-{N-[(6-amino-5-{[3-({[4-chloro-3-(trifluoromethyl)phenyl]amino}carbonyl)phenyl]ethynyl}pyridin-3-yl)carbonyl]sulfonimidoyl}dipentanoate,
Dimethyl 5,5'-{N-[(6-amino-5-{[3-({[(2-fluoro-5-methylphenyl)amino]carbonyl}amino)phenyl]ethynyl}pyridin-3-yl)carbonyl]sulfonimidoyl}dipentanoate,
Dimethyl 5,5'-{N-[(6-amino-5-{[4-({[(2-fluoro-5-methylphenyl)amino]carbonyl}amino)phenyl]ethynyl}pyridin-3-yl)carbonyl]sulfonimidoyl}dipentanoate,
Dimethyl 5,5'-(N-{[6-amino-5-({3-[(3-methyl-2-furoyl)amino]phenyl}ethynyl)pyridin-3-yl]carbonyl}sulfonimidoyl)diethanoate,
Dimethyl 5,5'-[N-({6-amino-5-[(3-{[(3-chloro-4-fluorophenyl)amino]carbonyl}phenyl)ethynyl]pyndin-3-yl}carbonyl)sulfonimidoyl]diethanoate, and
Dimethyl 5,5'-(N-{[6-amino-5-({3-[(3 methylbenzoyl)amino]phenyl}ethynyl) pyndin-3-yl]carbonyl}sulfonimidoyl)diethanoate; or a pharmaceutically acceptable salt thereof.

13. A compound having tyrosine kinase inhibiting activity that is a 2 and/or 6 amino, 5-arylethynyl, 3-carbonyl sulfonimidoyl pyridine, wherein said arylethynyl is substituted with an aryl group.
14. The compound of claim 13 wherein said sulfonimidoyl is a dialkyl dialkanoate ester.
15. The compound of claim 13 wherein said aryl substituent is linked to said arylethynyl group by a linking group represented by the formula —$(NH)_p$—C(O)—$(NH)_q$- wherein p is 0 or 1 and q is 0 or 1.
16. The compound of claim 15 wherein said arylethynyl is phenylethynyl.
17. The compound of claim 16 wherein said aryl substituent is selected from the group consisting of phenyl and furanyl.
18. The compound of claim 17 wherein said sulfonimidoyl is a dialkyl dialkanoate ester.

19. The compound of claim 18 wherein said aryl substituent is furanyl.

20. The compound of claim 18 wherein said aryl substituent is phenyl.

21. A method for treating a disease related to unregulated tyrosine kinase signal transduction, where the disease is selected from the group consisting of diabetic retinopathy, age-related macular degeneration, and retinopathy of prematurity, the method comprising the step of administering to a subject in need thereof a therapeutically effective amount of a compound represented by the general formula I:

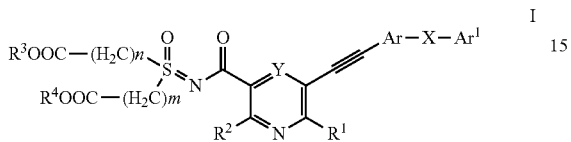

wherein;
R$^1$ is hydrogen or NH$_2$;
R$^2$ is hydrogen or NH$_2$;
X is selected from the group consisting of

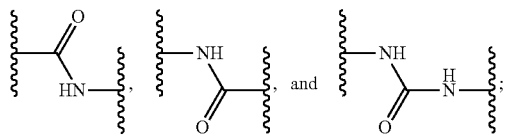

Y is CH or N;
Ar is an aryl group, wherein said aryl group may be optionally substituted with halogen, alkyl, alkoxy, or alkoxycarbonyl;
Ar$^1$ is an aryl group, wherein said aryl group may be optionally substituted with halogen, alkyl, alkoxy, alkoxycarbonyl, sulfinyl, thioether, fluoro or chloro-substituted lower alkyl;
R$^3$ is hydrogen or lower alkyl;
R$^4$ is hydrogen or lower alkyl;
n is an integer of from 1 to 6; and
m is an integer of from 1 to 6; or a pharmaceutically acceptable salt of said compound.

22. The method of claim 21 wherein Y is CH.

23. The method of claim 22 wherein Ar is phenyl.

24. The method of claim 23 wherein R1 is NH$_2$.

25. The method of claim 24 wherein R$^2$ is hydrogen.

26. The method of claim 25 wherein R$^3$ is methyl.

27. The method of claim 26 wherein R$^4$ is methyl.

28. The method of claim 27 wherein n is an integer of 1 or 4.

29. The method of claim 28 wherein m is an integer of 1 or 4.

30. The method of claim 29 wherein Ar$^1$ is selected from the group consisting of phenyl, furanyl and pyrrolyl, which is substituted with fluoro, chloro, lower alkyl, lower alkoxy, loweralkoxycarbonyl, lower alkylsulfinyl, lower alkylthioether, fluoro-substituted lower alkyl, or chloro-substituted lower alkyl.

31. The method of claim 30 wherein the substituent is selected from the group consisting of methyl, tertiary butyl, fluoro, chloro,trifluoromethyl, methoxy, methylsulfinyl, methylthioether and methoxycarbonyl.

32. The method of claim 21 wherein said compound is selected from the group consisting of Dimethyl 5,5'-(N-{[6-amino-5-({3-[(3-methylbenzoyl)amino]phenyl}ethynyl)pyridin-3-yl]carbonyl}sulfonimidoyl)dipentanoate, Dimethyl 5,5'-(N-{[6-amino-5-({3-[(3-methyl-2-furoyl)amino]phenyl}ethynyl)pyridin-3-yl]carbonyl}sulfonimidoyl)dipentanoate, Dimethyl 5,5'-[N-({6-amino-5-[(3-{[3-(methylthio)benzoyl]amino}phenyl)ethynyl]pyridin-3-yl}carbonyl)sulfonimidoyl]dipentanoate, Dimethyl 5,5'-(N-{[6-amino-5-({3-[(3-chloro-4-fluorobenzoyl)amino]phenyl}ethynyl)pyridin-3-yl]carbonyl}sulfonimidoyl)dipentanoate, Dimethyl 5,5'-[N-({6-amino-5-[(3-{[3-(trifluoromethyl)benzoyl]amino}phenyl)ethynyl]pyridin-3-yl}carbonyl)sulfonimidoyl]dipentanoate, Dimethyl 5,5'-(N-{[6-amino-5-({3-[(3-chlorobenzoyl)amino]phenyl}ethynyl)pyridin-3-yl]carbonyl}sulfonimidoyl)dipentanoate, Dimethyl 5,5'-(N-{[6-amino-5-({3-[(2-fluoro-5-methylbenzoyl)amino]phenyl}ethynyl)pyridin-3-yl]carbonyl}sulfonimidoyl)dipentanoate, Dimethyl 5,5'-[N-({6-amino-5-[(3-{[3-(methylsulfinyl)benzoyl]amino}phenyl)ethynyl]pyridin-3-yl}carbonyl)sulfonimidoyl]dipentanoate, Methyl3-{[(3-{[2-amino-5-({[bis(5-methoxy-5-oxopentyl)(oxido)-λ$^4$-sulfanylidene]amino}carbonyl)pyridin-3-yl]ethynyl}phenyl)amino]carbonyl}benzoate, Dimethyl 5,5'-[N-({6-amino-5-[(3-{[2-fluoro-5-(trifluoromethyl)benzoyl]amino}phenyl)ethynyl]pyridin-3-yl}carbonyl)sulfonimidoyl]dipentanoate, Dimethyl 5,5'-[N-({6-amino-5-[(3-{[(3-methoxyphenyl)amino]carbonyl}phenyl)ethynyl]pyridin-3-yl}carbonyl)sulfonimidoyl]dipentanoate, Dimethyl 5,5'-[N-({6-amino-5-[(3-{[(3-methylphenyl)amino]carbonyl}phenyl)ethynyl]pyridin-3-yl}carbonyl)sulfonimidoyl]dipentanoate, Dimethyl 5,5'-[N-({6-amino-5-[(3-{[(3-chloro-4-methoxyphenyl)amino]carbonyl}phenyl)ethynyl]pyridin-3-yl}carbonyl)sulfonimidoyl]dipentanoate, Dimethyl 5,5'-[N-({6-amino-5-[(3-{[(2-fluoro-5-methylphenyl)amino]carbonyl}phenyl)ethynyl]pyridin-3-yl}carbonyl)sulfonimidoyl]dipentanoate, Dimethyl 5,5'-[N-({6-amino-5-[(3-{[(3-chloro-4-fluorophenyl)amino]carbonyl}phenyl)ethynyl]pyridin-3-yl}carbonyl)sulfonimidoyl]dipentanoate, Dimethyl 5,5'-[N-({6-amino-5-[(3-{[(5-tert-butylisoxazol-3-yl)amino]carbonyl}phenyl)ethynyl]pyridin-3-yl}carbonyl)sulfonimidoyl]dipentanoate, Dimethyl 5,5'-{N-[(6-amino-5-{[3-({[4-chloro-3-(trifluoromethyl)phenyl]amino}carbonyl)phenyl]ethynyl}pyridin-3-yl)carbonyl]sulfonimidoyl}dipentanoate, Dimethyl 5,5'-{N-[(6-amino-5-{[3-({[(2-fluoro-5-methylphenyl)amino]carbonyl}amino)phenyl]ethynyl}pyridin-3-yl)carbonyl]sulfonimidoyl}dipentanoate, Dimethyl 5,5'-{N-[(6-amino-5-{[4-({[(2-fluoro-5-methylphenyl)amino]carbonyl}amino)phenyl]ethynyl}pyridin-3-yl)carbonyl]sulfonimidoyl}dipentanoate, Dimethyl 5,5'-(N-{[6-amino-5-({3-[(3-methyl-2-furoyl)amino]phenyl}ethynyl)pyridin-3-yl]carbonyl}sulfonimidoyl)diethanoate, Dimethyl 5,5'-[N-({6-amino-5-[(3-{[(3-chloro-4-fluorophenyl)amino]carbonyl}phenyl)ethynyl]pyridin-3-yl}carbonyl)sulfonimidoyl]diethanoate, and Dimethyl 5,5'-(N-{[6-amino-5-({3-[(3 methylbenzoyl)amino]phenyl}ethynyl) pyridin-3-yl]carbonyl}sulfonimidoyl)diethanoate; or a pharmaceutically acceptable salt thereof.

33. A pharmaceutical composition comprising at least one compound of claim 1 or a pharmaceutically acceptable salt thereof, and at least one pharmaceutically acceptable carrier.

34. A pharmaceutical composition comprising at least one compound of claim 12 or a pharmaceutically acceptable salt thereof, and at least one pharmaceutically acceptable carrier.

35. A pharmaceutical composition comprising at least one compound of claim 13 or a pharmaceutically acceptable salt thereof, and at least one pharmaceutically acceptable carrier.

* * * * *